United States Patent
Schoefl et al.

(10) Patent No.: US 9,743,674 B2
(45) Date of Patent: *Aug. 29, 2017

(54) COMBINATIONS COMPRISING A FUNGICIDAL STRAIN AND AN ACTIVE COMPOUND

(71) Applicant: Bayer CropScience LP, Research Triangle Park, NC (US)

(72) Inventors: Ulrich Schoefl, Apex, NC (US); Maria Scherer, Landau (DE); Egon Haden, Ludwigshafen (DE)

(73) Assignee: Bayer CropScience LP, Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/184,691

(22) Filed: Jun. 16, 2016

(65) Prior Publication Data

US 2016/0295869 A1    Oct. 13, 2016

Related U.S. Application Data

(63) Continuation of application No. 14/731,791, filed on Jun. 5, 2015, now Pat. No. 9,392,797, which is a continuation of application No. 12/678,543, filed as application No. PCT/EP2008/062279 on Sep. 16, 2008, now Pat. No. 9,078,447.

(30) Foreign Application Priority Data

Sep. 20, 2007 (EP) .................................. 07116844

(51) Int. Cl.
| | | |
|---|---|---|
| A01N 63/00 | (2006.01) |
| A01N 63/02 | (2006.01) |
| A01N 47/12 | (2006.01) |
| A01N 27/00 | (2006.01) |
| A01N 31/08 | (2006.01) |
| A01N 31/10 | (2006.01) |
| A01N 33/06 | (2006.01) |
| A01N 35/04 | (2006.01) |
| A01N 37/44 | (2006.01) |
| A01N 43/40 | (2006.01) |
| A01N 43/50 | (2006.01) |
| A01N 43/54 | (2006.01) |
| A01N 43/56 | (2006.01) |
| A01N 43/60 | (2006.01) |
| A01N 43/653 | (2006.01) |
| A01N 43/76 | (2006.01) |
| A01N 43/78 | (2006.01) |
| A01N 43/84 | (2006.01) |
| A01N 43/90 | (2006.01) |
| A01N 45/00 | (2006.01) |
| A01N 47/40 | (2006.01) |
| A01N 55/00 | (2006.01) |
| A01N 55/02 | (2006.01) |

(52) U.S. Cl.
CPC ............ *A01N 63/00* (2013.01); *A01N 27/00* (2013.01); *A01N 31/08* (2013.01); *A01N 31/10* (2013.01); *A01N 33/06* (2013.01); *A01N 35/04* (2013.01); *A01N 37/44* (2013.01); *A01N 43/40* (2013.01); *A01N 43/50* (2013.01); *A01N 43/54* (2013.01); *A01N 43/56* (2013.01); *A01N 43/60* (2013.01); *A01N 43/653* (2013.01); *A01N 43/76* (2013.01); *A01N 43/78* (2013.01); *A01N 43/84* (2013.01); *A01N 43/90* (2013.01); *A01N 45/00* (2013.01); *A01N 47/12* (2013.01); *A01N 47/40* (2013.01); *A01N 55/00* (2013.01); *A01N 55/02* (2013.01); *A01N 63/02* (2013.01)

(58) Field of Classification Search
None
See application file for complete search history.

(56) References Cited

FOREIGN PATENT DOCUMENTS

JP      2006-347885 A      12/2006

OTHER PUBLICATIONS

Edgecomb, D.W., "Challenges to Bio-Pesticide Global Registration and Adoption—a Manufacturer's Perspective: 'Bio-Pesticides: The Way Ahead' Oct. 18, 2006".

Zitter, T.A., "Control of Early Blight of Tomato with Genetic Resistance and Conventional and Biological Sprays," Acta Hort. 695, ISHS 2005 (Proc. 1st IS on Tomato Diseases, ed. M. T. Momol et al.) (2005), pp. 181-190.

*Primary Examiner* — Jennifer Graser
(74) *Attorney, Agent, or Firm* — Adam L. Lunceford; Michelle L. Samonek

(57) ABSTRACT

Fungicidal mixtures, comprising 1) a fungicidal strain (I) selected from a) the *Bacillus substilis* strain with NRRL Accession No. B-21661, and b) the *Bacillus pumilus* strain with NRRL Accession No. B-30087, or a mutant of these strains having all the identifying characteristics of the respective strain, or a metabolite produced by the respective strain that exhibits activity against plant pathogenic fungi, and 2) at least one chemical compound (II), selected from the active compound groups A) to F): A) azoles; B) strobilurins; C) carboxamides; D) heterocyclic compounds; E) carbamates; F) other fungicides; in a synergistically effective amount, methods for controlling harmful fungi using compositions of components 1) and 2), the use of a component 1) with a component 2) for preparing such compositions, and also fungicidal agents and seed comprising such compositions.

18 Claims, No Drawings

COMBINATIONS COMPRISING A FUNGICIDAL STRAIN AND AN ACTIVE COMPOUND

CROSS-REFERENCE TO RELATED APPLICATION(S)

This application is a continuation of U.S. patent application Ser. No. 14/731,791, filed Jun. 5, 2015, which is a continuation of U.S. patent application Ser. No. 12/678,543, filed Mar. 17, 2010, which is a National Stage application of International Application No. PCT/EP2008/062279, filed Sep. 16, 2008, the entire contents of which is hereby incorporated herein by reference. This application also claims the benefit under 35 U.S.C. §119 of European Patent Application No. 07116844.7, filed Sep. 20, 2007, the entire contents of which is hereby incorporated herein by reference.

The present invention relates to fungicidal compositions for controlling phytopathogenic harmful fungi comprising, as active components, 1) a fungicidal strain (I) selected from
   a) the *Bacillus substilis* strain with NRRL Accession No. B-21661, and
   b) the *Bacillus pumilus* strain with NRRL Accession No. B-30087, or a mutant of these strains having all the identifying characteristics of the respective strain, or a metabolite produced by the respective strain that exhibits its activity against plant pathogenic fungi;
and
2) at least one chemical compound (II), selected from the active compound groups A) to F):

A) azoles selected from the group consisting of azaconazole, diniconazole-M, oxpoconazol, paclobutrazol, uniconazol, 1-(4-chloro-phenyl)-2-([1,2,4]triazol-1-yl)-cycloheptanol and imazalil-sulfphate;

B) strobilurins selected from the group consisting of 2-(2-(6-(3-chloro-2-methyl-phenoxy)-5-fluoro-pyrimidin-4-yloxy)-phenyl)-2-methoxyimino-N-methyl-acetamide and 3-methoxy-2-(2-(N-(4-methoxy-phenyl)-cyclo-propanecarboximidoylsulfanylmethyl)-phenyl)-acrylic acid methyl ester;

C) carboxamides selected from the group consisting of benalaxyl, benalaxyl-M, 2-amino-4-methyl-thiazole-5-carboxamide, 2-chloro-N-(1,1,3-trimethyl-indan-4-yl)-nicotinamide, N-(2-(1,3-dimethylbutyl)-phenyl)-1,3-dimethyl-5-fluoro-1H-pyrazole-4-carboxamide, N-(4'-chloro-3',5-difluoro-biphenyl-2-yl)-3-difluoromethyl-1-methyl-1H-pyrazole-4-carboxamide, N-(4'-chloro-3',5-difluoro-biphenyl-2-yl)-3-trifluoromethyl-1-methyl-1H-pyrazole-4-carboxamide, N-(cis-2-bicyclopropyl-2-yl-phenyl)-3-difluoromethyl-1-methyl-1H-pyrazole-4-carboxamide, N-(trans-2-bicyclopropyl-2-yl-phenyl)-3-difluoromethyl-1-methyl-1H-pyrazole-4-carboxamide, fluopyram, N-(3-ethyl-3,5-5-trimethyl-cyclohexyl)-3-formylamino-2-hydroxy-benzamide, oxytetracyclin, silthiofam, N-(6-methoxypyridin-3-yl) cyclopropanecarboxylic acid amide, penthiopyrad, isopyrazam and a 1-methyl-pyrazol-4-ylcarboxamide of the formula III

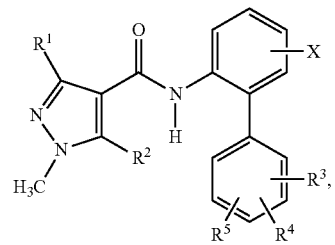

in which the substituents are as defined below:
X is hydrogen or fluorine;
$R^1$ is $C_1$-$C_4$-alkyl or $C_1$-$C_4$-haloalkyl;
$R^2$ is hydrogen or halogen;
$R^3$, $R^4$ and $R^5$ independently of one another are hydrogen, cyano, nitro, halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio or $C_1$-$C_4$-haloalkyl;

D) heterocyclic compounds selected from the group consisting of 5-chloro-7-(4-methylpiperidin-1-yl)-6-(2,4,6-trifluorophenyl)-[1,2,4]triazolo[1,5-a]pyrimidine, 2,3,5,6-tetrachloro-4-methanesulfonyl-pyridine, 3,4,5-trichloro-pyridine-2,6-di-carbonitrile, N-(1-(5-bromo-3-chloro-pyridin-2-yl)-ethyl)-2,4-dichloro-nicotinamide, N-((5-bromo-3-chloro-pyridin-2-yl)-methyl)-2,4-dichloro-nicotinamide, diflumetorim, nitrapyrin, dodemorph-acetate, fluoroimid, blasticidin-S, chinomethionat, debacarb, oxolinic acid, piperalin and an azolopyrimidin-7-ylamine of the formula IV

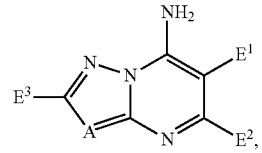

in which the substituents have the following meanings:
$E^1$ is $C_3$-$C_{12}$-alkyl, $C_2$-$C_{12}$-alkenyl, $C_5$-$C_{12}$-alkoxyalkyl, $C_3$-$C_6$-cycloalkyl, phenyl or phenyl-$C_1$-$C_4$-alkyl;
$E^2$ is $C_1$-$C_{12}$-alkyl, $C_2$-$C_{12}$-alkenyl, $C_1$-$C_4$-haloalkyl or $C_1$-$C_4$-alkoxy-$C_1$-$C_4$-alkyl;
where the aliphatic chains in $E^1$ and/or $E^2$ may be substituted by one to four identical or different groups $R^a$:
$R^a$ is halogen, cyano, hydroxyl, mercapto, $C_1$-$C_{10}$-alkyl, $C_1$-$C_{10}$-haloalkyl, $C_3$-$C_8$-cycloalkyl, $C_2$-$C_{10}$-alkenyl, $C_2$-$C_{10}$-alkynyl, $C_1$-$C_6$-alkoxy, $C_1$-$C_6$-alkylthio, $C_1$-$C_6$-alkoxy-$C_1$-$C_6$-alkyl or $NR^A R^B$;
$R^A$, $R^B$ independently of one another are hydrogen or $C_1$-$C_6$-alkyl;
where the cyclic groups in $E^1$ and/or $R^a$ may be substituted by one to four groups $R^b$:
$R^b$ is halogen, cyano, hydroxyl, mercapto, nitro, $NR^A R^B$, $C_1$-$C_{10}$-alkyl, $C_1$-$C_6$-haloalkyl, $C_2$-$C_6$-alkenyl, $C_2$-$C_6$-alkynyl or $C_1$-$C_6$-alkoxy;
$E^3$ is hydrogen, halogen, cyano, $NR^A R^B$, hydroxyl, mercapto, $C_1$-$C_6$-alkyl, $C_1$-$C_6$-haloalkyl, $C_3$-$C_8$-cycloalkyl, $C_1$-$C_6$-alkoxy, $C_1$-$C_6$-alkylthio, $C_3$-$C_8$-cycloalkoxy, $C_3$-$C_8$-cycloalkylthio, carboxyl, formyl, $C_1$-$C_{10}$-alkylcarbonyl, $C_1$-$C_{10}$-alkoxycarbonyl, $C_2$-$C_{10}$-alkenyloxycarbonyl, $C_2$-$C_{10}$-alkynyloxycarbonyl, phenyl, phenoxy, phenylthio, benzyloxy, benzylthio or $C_1$-$C_6$-alkyl-S(O)$_m$—;

m is 0, 1 or 2;

A is CH or N;

E) carbamates selected from the group consisting of methasulphocarb and propamocarb hydrochlorid;

F) other fungicides selected from the group consisting of metrafenone, dodine free base, guazatine-acetate, iminoctadine-triacetate, iminoctadine-tris(albesilate), kasugamycin-hydrochlorid-hydrat, dichlorophen, pentachlorophenol and its salts, N-(4-chloro-2-nitro-phenyl)-N-ethyl-4-methyl-benzenesulfon-amide, dicloran, nitrothal-isopropyl, tecnazen, biphenyl, bronopol, diphenylamine, mildiomycin, oxin-copper, prohexadione calcium, N-(cyclopropylmethoxyimino-(6-difluoromethoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluormethyl-4-(3-trimethylsilanyl-propoxy)-phenyl)-N-ethyl-N-methyl formamidine and N'-(5-difluoromethyl-2-methyl-4-(3-trimethylsilanyl-propoxy)-phenyl)-N-ethyl-N-methyl formamidine;

in a synergistically effective amount.

Moreover, the invention relates to a method for controlling harmful fungi using a composition of components 1) and 2), to the use of a component 1) with a component 2) for preparing such compositions, and also to agents and seed comprising such compositions.

The strains (I), their mutants and the metabolites produced by the strains that exhibit activity against plant pathogenic fungi, referred to above as component 1), their preparation and their action against harmful fungi are known from WO 98/50422, WO 00/29426 and WO 00/58442, therein also referred to as AQ713 (QST713) and QST2808.

Isolates of bacteria of species *Bacillus subtilis* and *Bacillus pumilus* which are effective in inhibiting the growth of fungi of species *botrytis cinerea* and/or *Alternaria brassicicola* and a method of obtaining those isolates are also known from WO 93/18654.

Example 13 of WO 98/50422 already discloses that synergistic activity is obtained by the combined treatment of component 1) a) and azoxystrobin.

NRRL is the abbreviation for the Agricultural Research Service Culture Collection, an international depositary authority for the purposes of deposing microorganism strains under the BUDAPEST TREATY ON THE INTERNATIONAL RECOGNITION OF THE DEPOSIT OF MICROORGANISMS FOR THE PURPOSES OF PATENT PROCEDURE, having the address National Center for Agricultural Utilization Research, Agricultural Research Service, U.S. Department of Agriculture, 1815 North University Street, Peoria, Ill. 61604, USA.

Suitable formulations of the *Bacillus subtilis* strain 1) a) are commercially available under the tradenames RHAPSODY®, SERENADE® MAX and SERENADE® ASO from AgraQuest, Inc., USA.

Suitable formulations of the *Bacillus pumilus* strain 1) b) are commercially available under the tradenames SONATA® and BALLAD® Plus from AgraQuest, Inc., USA.

However, the known strains (I), their mutants and the metabolites produced by the strains are, in particular at low application rates, not entirely satisfactory.

The active compounds (II) mentioned above as component 2), their preparation and their action against harmful fungi are generally known (cf., for example, http://www.h-clrss.demon.co.uk/index.html); they are commercially available.

N-(2-bicycloprop-2-yl-phenyl)-3-difluoromethyl-1-methyl-1H-pyrazole-4-carboxamide is known from WO 03/074491 and can be prepared in the manner described therein. The fungicidal activity of said compound against various harmful fungi is known from WO 2006/015866.

Isopyrazam is known from WO 04/035589 and can be prepared in the manner described therein or as described in WO 2007/068417.

The 1-methyl-pyrazol-4-ylcarboxanilides of formula (III) are known from the literature (cf., for example, EP-A 545 099, EP-A 589 301, WO 99/09013, WO 2003/70705 and WO 2006/087343), or they can be prepared in the manner described therein.

The azolopyrimidin-7-ylamines IV, their preparation and their action against harmful fungi are known from the literature (EP-A 71 792; EP-A 141 317; WO 03/009687; WO 05/087771; WO 05/087772; WO 05/087773; WO 2005/087772; WO 2006/087325; WO 2006/092428).

Metrafenone, 3'-bromo-2,3,4,6'-tetramethoxy-2',6-dimethylbenzophenone, is known from U.S. Pat. No. 5,945,567.

It was an object of the present invention, with a view to reducing the application rates and broadening the activity spectrum of the strains (I) and compounds (II), to provide compositions which, at a reduced total amount of active compounds applied, have improved activity against harmful fungi, in particular for certain indications.

We have accordingly found that this object is achieved by the compositions, of components 1) and 2), defined at the outset. Moreover, we have found that simultaneous, that is joint or separate, application of components 1) and 2) or successive application of the components 1) and 2) allows better control of harmful fungi than is possible with the strains, their mutants and the metabolites produced by the strains on the one hand and with the individual compounds (II) on the other hand, alone (synergistic mixtures).

By simultaneous, that is joint or separate, application of components 1) and 2), the fungicidal activity is increased in a superadditive manner.

Component 1) embraces not only the isolated, pure cultures of the *Bacillus substilis* strain and the *Bacillus pumilus* strain, but also their suspensions in a whole broth culture or as a metabolite-containing supernatant or a purified metabolite obtained from a whole broth culture of the strain.

"Whole broth culture" refers to a liquid culture containing both cells and media.

"Supernatant" refers to the liquid broth remaining when cells grown in broth are removed by centrifugation, filtration, sedimentation, or other means well known in the art.

The term "metabolite" refers to any compound, substance or byproduct of a fermentation or a microorganism that has fungicidal activity.

Preferred component 1) is a fungicidal strain 1) a), the *Bacillus substilis* strain with NRRL Accession No. B-21661, a mutant thereof having all the identifying characteristics of the strain, or a metabolite produced by the strain that exhibits activity against plant pathogenic fungi.

Many of the active compounds II can be present in different crystal modifications, which may differ in biological activity. They also form part of component 2).

Preference is given to compositions of a component 1) with a component 2) consisting of at least one active compound (II) selected from the group of A) azoles.

Preference is also given to compositions of a component 1) with a component 2) consisting of at least one active compound (II) selected from the group of B) strobilurins.

Preference is given to compositions of a component 1) with a component 2) consisting of at least one active compound (II) selected from the group of C) carboxamides.

Among the group of C) carboxamides, penthiopyrad, N-(2-(1,3-dimethylbutyl)-phenyl)-1,3-dimethyl-5-fluoro-1H-pyrazole-4-carboxamide, N-(cis-2-bicyclopropyl-2-yl-phenyl)-3-difluoromethyl-1-methyl-1H-pyrazole-4-carboxamide, N-(trans-2-bicyclopropyl-2-yl-phenyl)-3-difluoromethyl-1-methyl-1H-pyrazole-4-carboxamide and the 1-methyl-pyrazol-4-ylcarboxanilides of the formula III are preferred.

In the formula III, halogen is fluorine, chlorine, bromine or iodine, preferably fluorine or chlorine;

$C_1$-$C_4$-alkyl is methyl, ethyl, n-propyl, 1-methylethyl, n-butyl, 1-methylpropyl, 2-methylpropyl or 1,1-dimethylethyl, preferably methyl or ethyl;

$C_1$-$C_4$-haloalkyl is a partially or fully halogenated $C_1$-$C_4$-alkyl radical, where the halogen atom(s) is/are in particular fluorine, chlorine and/or bromine, i.e., for example, chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, heptafluoropropyl or nonafluorobutyl, in particular halomethyl, with particular preference $CH_2$—Cl, $CH(Cl)_2$, $CH_2$—F, $CHF_2$, $CF_3$, CHFCl, $CF_2$Cl or $CF(Cl)_2$, in particular $CHF_2$ or $CF_3$;

$C_1$-$C_4$-alkoxy is $OCH_3$, $OC_2H_5$, $OCH_2$—$C_2H_5$, OCH$(CH_3)_2$, n-butoxy, $OCH(CH_3)$—$C_2H_5$, $OCH_2$—$CH(CH_3)_2$ or $OC(CH_3)_3$, preferably $OCH_3$ or $OC_2H_5$;

$C_1$-$C_4$-haloalkoxy is a partially or fully halogenated $C_1$-$C_4$-alkoxy radical, where the halogen atom(s) is/are in particular fluorine, chlorine and/or bromine, i.e., for example, chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, heptafluoropropoxy or nonafluorobutoxy, in particular halomethoxy, particularly preferably $OCH_2$—Cl, $OCH(Cl)_2$, $OCH_2$—F, $OCH(F)_2$, $OCF_3$, OCHFCl, $OCF_2$Cl or $OCF(Cl)_2$;

$C_1$-$C_4$-alkylthio is $SCH_3$, $SC_2H$, $SCH_2$—$C_2H_5$, SCH$(CH_3)_2$, n-butylthio, $SCH(CH_3)$—$C_2H_5$, $SCH_2$—$CH(CH_3)_2$ or $SC(CH_3)_3$, preferably $SCH_3$ or $SC_2H_5$.

$C_1$-$C_4$-haloalkylthio is a partially or fully halogenated $C_1$-$C_4$-alkylthio radical, where the halogen atom(s) is/are in particular fluorine, chlorine and/or bromine, i.e., for example, chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio, pentafluoroethylthio, heptafluoropropylthio or nonafluorobutylthio, in particular halomethylthio, particularly preferably $SCF_3$;

Preferred 1-methylpyrazol-4-ylcarboxanilides III are, on the one hand, those in which X is hydrogen.

On the other hand, preferred compounds III are those in which X is fluorine.

For the mixtures according to the invention, preference is given to compounds of the formula III in which $R^1$ is methyl or halomethyl, in particular $CH_3$, $CHF_2$, $CH_2F$, $CF_3$, CHFCl or $CF_2$Cl.

Preference is furthermore given to compounds III in which $R^2$ is hydrogen, fluorine or chlorine, in particular hydrogen.

Preference is furthermore given to those compounds III in which $R^3$ is halogen, $C_1$-$C_4$-alkyl. $C_1$-$C_4$-haloalkyl, $C_1$-$C_4$-alkoxy, $C_1$-$C_4$-haloalkoxy or $C_1$-$C_4$-alkylthio, preferably halogen, methyl, halomethyl, methoxy, halomethoxy or methylthio, in particular F, Cl, $CH_3$, $CF_3$, $OCH_3$, $OCHF_2$, $OCF_3$ or $SCH_3$, particularly preferably fluorine.

Moreover, preference is given to those compounds III in which $R^4$ is halogen, in particular fluorine.

Preference is furthermore given to those compounds III in which $R^5$ is halogen, in particular fluorine.

Among those 1-methylpyrazol-4-ylcarboxanilides III where X is hydrogen, particular preference is given to N-(2'-fluoro-4'-chloro-5'-methoxybiphenyl-2-yl)-3-trifluoromethyl-1-methyl-1H-pyrazole-4-carboxamide, N-(2'-fluoro-4'-chloro-5'-methylbiphenyl-2-yl)-3-trifluoromethyl-1-methyl-1H-pyrazole-4-carboxamide, N-(3',4',5'-trifluorobiphenyl-2-yl)-3-trifluoromethyl-1-methyl-1H-pyrazole-4-carboxamide. N-(2',4',5'-trifluorobiphenyl-2-yl)-3-trifluoromethyl-1-methyl-1H-pyrazole-4-carboxamide. N-(2'-fluoro-4'-chloro-5'-methoxybiphenyl-2-yl)-3-difluoromethyl-1-methyl-1H-pyrazole-4-carboxamide, N-(2',3',4'-trifluorophenyl-2-yl)-3-trifluoromethyl-1-methyl-1H-pyrazole-4-carboxamide, N-(2'-fluoro-4'-chloro-5-methylbiphenyl-2-yl)-3-difluoromethyl-1-methyl-1H-pyrazole-4-carboxamide, N-(3',4',5'-trifluorobiphenyl-2-yl)-3-difluoromethyl-1-methyl-1H-pyrazole-4-carboxamide, N-(2',4',5'-trifluorobiphenyl-2-yl)-3-difluoromethyl-1-methyl-1H-pyrazole-4-carboxamide, N-(3',4',5'-trifluorobiphenyl-2-yl)-3-fluoromethyl-1-methyl-1H-pyrazole-4-carboxamide, N-(3',4',5'-trifluorobiphenyl-2-yl)-3-chlorodifluoromethyl-1-methyl-1H-pyrazole-4-carboxamide, N-(3',4',5'-trifluorobiphenyl-2-yl)-3-chlorofluoromethyl-1-methyl-1H-pyrazole-4-carboxamide, N-(2',3',4'-trifluorobiphenyl-2-yl)-3-fluoromethyl-1-methyl-1H-pyrazole-4-carboxamide, N-(2',4',5'-trifluorobiphenyl-2-yl)-3-fluoromethyl-1-methyl-1H-pyrazole-4-carboxamide, N-(4'-trifluoromethylthio-biphenyl-2-yl)-3-difluoromethyl-1-methyl-1H-pyrazole-4-carboxamide and N-(4'-trifluoromethylthio-biphenyl-2-yl)-1-methyl-3-trifluoromethyl-1H-pyrazole-4-carboxamide.

Among those 1-methylpyrazol-4-ylcarboxanilides I where X is fluorine, particular preference is given to N-(3',4'-dichloro-3-fluorobiphenyl-2-yl)-1-methyl-3-trifluoromethyl-1H-pyrazole-4-carboxamide, N-(3',4'-dichloro-3-fluorobiphenyl-2-yl)-1-methyl-3-difluoromethyl-1H-pyrazole-4-carboxamide, N-(3',4'-difluoro-3-fluorobiphenyl-2-yl)-1-methyl-3-trifluoromethyl-1H-pyrazole-4-carboxamide, N-(3',4'-difluoro-3-fluorobiphenyl-2-yl)-1-methyl-3-difluoromethyl-1H-pyrazole-4-carboxamide, N-(3'-chloro-4'-fluoro-3-fluorobiphenyl-2-yl)-1-methyl-3-difluoromethyl-1H-pyrazole-4-carboxamide, N-(3',4'-dichloro-4-fluorobiphenyl-2-yl)-1-methyl-3-trifluoromethyl-1H-pyrazole-4-carboxamide, N-(3',4'-difluoro-4-fluorobiphenyl-2-yl)-1-methyl-3-trifluoromethyl-1H-pyrazole-4-carboxamide, N-(3',4'-dichloro-4-fluorobiphenyl-2-yl)-1-methyl-3-difluoromethyl-1H-pyrazole-4-carboxamide. N-(3',4'-difluoro-4-fluorobiphenyl-2-yl)-1-methyl-3-difluoromethyl-1H-pyrazole-4-carboxamide, N-(3'-chloro-4'-fluoro-4- fluorobiphenyl-2-yl)-1-methyl-3-difluoromethyl-1H-pyrazole-4-carboxamide, N-(3',4'-dichloro-5-fluorobiphenyl-2-yl)-1-methyl-3-trifluoromethyl-1H-pyrazole-4-carboxamide, N-(3',4'-difluoro-5-fluorobiphenyl-2-yl)-1-methyl-3-trifluoromethyl-1H-pyrazole-4-carboxamide, N-(3',4-dichloro-5-fluorobiphenyl-2-yl)-1-methyl-3-difluoromethyl-1H-pyrazole-4-carboxamide, N-(3',4'-difluoro-5-fluorobiphenyl-2-yl)-1-methyl-3-difluoromethyl-1H-pyrazole-4-carboxamide, N-(3',4'-dichloro-5-fluorobiphenyl-2-yl)-1,3-dimethyl-1H-pyrazole-4-carboxamide, N-(3'-chloro-4'-fluoro-5-fluorobiphenyl-2-yl)-1-methyl-3-difluoromethyl-1H-pyrazole-4-carboxamide, N-(4'-fluoro-4-fluorobiphenyl-2-yl)-1-methyl-3-trifluoromethyl-1H-pyrazole-4-carboxamide, N-(4'-fluoro-5-fluorobiphenyl-2-yl)-1-methyl-3-trifluoromethyl-1H-pyrazole-4-carboxamide, N-(4'-chloro-5-fluorobiphenyl-2-yl)-1-methyl-3-trifluoromethyl-1H-pyrazole-4-carboxamide, N-(4'-methyl-5-fluorobiphenyl-2-yl)-1-methyl-3-trifluoromethyl-1H-pyrazole-4-carboxamide, N-(4'-fluoro-5-fluorobiphenyl-2-yl)-1,3-dimethyl-1H-pyrazole-4-carboxamide, N-(4'-chloro-5-fluorobiphenyl-2-yl)-1,3-dimethyl-1H-pyrazole-4-carboxamide, N-(4'-methyl-5-fluorobiphenyl-2-yl)-1,3-dimethyl-1H-pyrazole-4-carboxamide, N-(4'-fluoro-6-fluorobiphenyl-2-yl)-1-methyl-3-trifluoromethyl-1H-pyrazole-4-carboxamide and N-(4'-chloro-6-fluorobiphenyl-2-yl)-1-methyl-3-trifluoromethyl-1H-pyrazole-4-carboxamide.

Preference is furthermore also given to compositions of a component 1) with a component 2) consisting of at least one active compound (II) selected from the group of D) heterocyclic compounds.

Among the D) heterocyclic compounds, 5-chloro-7-(4-methylpiperidin-1-yl)-6-(2,4,6-trifluorophenyl)-[1,2,4]triazolo[1,5-a]pyrimidine and the azolopyrimidin-7-ylamines of the formula IV are preferred.

In the formula IV, halogen is fluorine, chlorine, bromine or iodine.

alkyl: saturated, straight-chain or branched hydrocarbon radicals having 1 to 4, 1 to 6, 1 to 10, 1 to 12 or 3 to 12 carbon atoms, for example $C_1$-$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

haloalkyl: straight-chain or branched alkyl radicals having 1 to 4, 1 to 6 or 1 to 10 carbon atoms (as mentioned above), where some or all of the hydrogen atoms in these radicals may be replaced by halogen atoms as mentioned above: in particular $C_1$-$C_2$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl or 1,1,1-trifluoroprop-2-yl;

alkenyl: unsaturated straight-chain or branched hydrocarbon radicals having 2 to 6, 2 to 10 or 2 to 12 carbon atoms and one or two double bonds in any position, for example $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl or 1-ethyl-2-methyl-2-propenyl;

alkynyl: straight-chain or branched hydrocarbon radicals having 2 to 6 or 2 to 10 carbon atoms and one or two triple bonds in any position, for example $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl or 1-ethyl-1-methyl-2-propynyl;

cycloalkyl: mono- or bicyclic saturated hydrocarbon radicals having 3 to 6 or 3 to 8 carbon ring members, for example $C_3$-$C_8$-cycloalkyl, such as cyclopropyl, cyclobutyl, cyclopentyl, cyclohexyl, cycloheptyl or cyclooctyl;

cycloalkoxy: mono- or bicyclic saturated hydrocarbon radicals which are attached via an oxygen atom (—O—);

cycloalkylthio: mono- or bicyclic, saturated hydrocarbon radicals which are attached via a sulfur atom (—S—);

alkylthio: saturated, straight-chain or branched hydrocarbon radicals which are attached via a sulfur atom (—S—);

alkylcarbonyl: straight-chain or branched alkyl radicals which have 1 to 10 carbon atoms and are attached via a carbonyl group (—CO—);

alkoxy: straight-chain or branched alkyl radicals which are attached via an oxygen atom (—O—);

alkoxyalkyl: straight-chain or branched alkoxy radicals which are attached to an alkyl radical;

haloalkoxy: straight-chain or branched alkoxy radicals, where some or all of the hydrogen atoms in these radicals may be replaced by halogen;

alkoxycarbonyl: alkoxy radicals which have 1 to 10 carbon atoms and are attached via a carbonyl group (—CO—);

alkenyloxycarbonyl: alkenyl radicals which are attached via an oxygen atom (—O—) to a carbonyl group (—CO—);

alkynyloxycarbonyl: alkynyl radicals which are attached via an oxygen atom (—O—) to a carbonyl group (—CO—);

phenylalkyl: a phenyl group which is attached via saturated, straight-chain or branched alkyl radicals.

Preferred azolopyrimidin-7-ylamines IV are those compounds in which $E^1$ is straight-chain or branched $C_3$-$C_{12}$-alkyl or phenyl which may be substituted by one to three halogen or $C_1$-$C_4$-alkyl groups.

In one embodiment of the compounds IV, the aliphatic chains in $E^1$ and $E^2$ or in $E^1$ or $E^2$ are not substituted by $R^a$.

A preferred embodiment relates to compounds IV in which $E^1$ is straight-chain or branched $C_5$-$C_{10}$-alkyl, in particular ethyl, 3,5,5-trimethylhexyl, n-heptyl, n-octyl, n-nonyl or n-decyl.

A further embodiment relates to compounds IV in which $E^1$ is phenyl which is unsubstituted or substituted by one to four radicals $R^b$.

Preferred compounds IV are those in which $E^1$ is a substituted phenyl group which corresponds to a group Ar

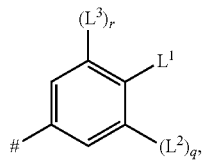

in which
$L^1$ to $L^3$ are halogen, cyano, hydroxyl, mercapto, nitro, $NR^AR^B$, $C_1$-$C_{10}$-alkyl, $C_1$-$C_6$-haloalkyl, $C_2$-$C_6$-alkenyl, $C_2$-$C_6$-alkynyl or $C_1$-$C_6$-alkoxy; r and q Independently of one another may be 0 or 1 sein, where $NR^AR^B$ is as defined in formula IV and #denotes the bond to the azolopyrimidine skeleton.

In a further embodiment of the compounds IV, $L^1$ is halogen, cyano, hydroxyl, mercapto, nitro, $NR^AR^B$, $C_1$-$C_6$-alkyl, halomethyl and $C_1$-$C_2$-alkoxy, preferably halogen, cyano, $C_1$-$C_6$-alkyl, halomethyl or $C_1$-$C_2$-alkoxy.

In a further embodiment of the compounds IV, q is 0 or $L^2$ is one of the groups mentioned above and q is 1.

In a further embodiment of the compounds IV, r is 0 or $L^3$ is halogen, cyano, hydroxyl, mercapto, nitro, $NR^AR^B$, $C_1$-$C_6$-alkyl, halomethyl or $C_1$-$C_2$-alkoxy and r is 1.

Preferably, r is zero.

Preference is given to compounds IV in which $E^2$ is straight-chain or branched $C_1$-$C_2$-alkyl, $C_1$-$C_4$-alkoxy-$C_1$-$C_4$-alkyl or $C_1$-$C_4$-haloalkyl.

In a particularly preferred embodiment of the compounds IV, $E^2$ is methyl, ethyl, n-propyl, n-octyl, trifluoromethyl or methoxymethyl, in particular methyl, ethyl, trifluoromethyl or methoxymethyl.

Preference is furthermore given to compounds IV in which $E^3$ is hydrogen.

In a further embodiment of the compounds IV, $E^3$ is amino.

One embodiment of the compounds IV relates to those in which A is N. These compounds correspond to formula IVa in which the variables are as defined for formula IV:

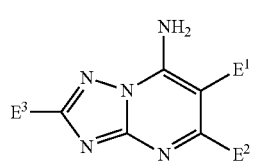

Another embodiment of the compounds of the formula IV relates to those in which A is CH. These compounds correspond to formula IVb in which the variables are as defined for formula IV:

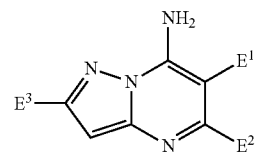

In a further embodiment of preferred compounds IV, the sum of the carbon atoms in the carbon radicals of $E^1$ and $E^2$ is not more than 12.

Very particularly preferred azolopyrimidin-7-ylamines IV are those listed in Table 1:

TABLE 1

| No. | Compound |
|---|---|
| IV.1 | 6-(3,4-dichlorophenyl)-5-methyl-[1,2,4]triazolo[1,5-a]pyrimidin-7-ylamine |
| IV.2 | 6-(4-tert-butylphenyl)-5-methyl-[1,2,4]triazolo[1,5-a]pyrimidin-7-ylamine |
| IV.3 | 5-methyl-6-(3,5,5-trimethylhexyl)-[1,2,4]triazolo[1,5-a]pyrimidin-7-ylamine |
| IV.4 | 5-methyl-6-octyl-[1,2,4]triazolo[1,5-a]pyrimidin-7-ylamine |
| IV.5 | 5-ethyl-6-octyl-[1,2,4]triazolo[1,5-a]pyrimidin-2,7-diamine |
| IV.6 | 6-ethyl-5-octyl-[1,2,4]triazolo[1,5-a]pyrimidin-7-ylamine |
| IV.7 | 5-ethyl-6-octyl-[1,2,4]triazolo[1,5-a]pyrimidin-7-ylamine |
| IV.8 | 5-ethyl-6-(3,5,5-trimethylhexyl)-[1,2,4]triazolo[1,5-a]pyrimidin-7-ylamine |
| IV.9 | 6-octyl-5-propyl-[1,2,4]triazolo[1,5-a]pyrimidin-7-ylamine |
| IV.10 | 5-methoxymethyl-6-octyl-[1,2,4]triazolo[1,5-a]pyrimidin-7-ylamine |
| IV.11 | 6-octyl-5-trifluoromethyl-[1,2,4]triazolo[1,5-a]pyrimidin-7-ylamine |
| IV.12 | 5-trifluoromethyl-6-(3,5,5-trimethylhexyl)-[1,2,4]triazolo[1,5-a]pyrimidin-7-ylamine |

Preference is furthermore also given to compositions of a component 1) with a component 2) consisting of at least one active compound (II) selected from the group of E) carbamates.

Preference is furthermore also given to compositions of a component 1) with a component 2) consisting of at least one active compound (II) selected from the group of F) other fungicides.

Preference is also given to compositions of a component 1) with a component 2) consisting of at least one active compound (II) selected from the group of F) other fungicides selected from the group consisting of metrafenone, dodine free base, guazatine-acetate, iminoctadine-triacetate, iminoctadine-tris(albesilate), kasugamycin-hydrochloridhydrat, dichlorophen, pentachlorophenol and its salts, N-(4-chloro-2-nitro-phenyl)-N-ethyl-4-methyl-benzenesulfonamide, dicloran, nitrothal-isopropyl, tecnazen, biphenyl, bronopol, diphenylamine, mildiomycin, oxin-copper and prohexadione calcium, in particular metrafenone, dodine free base, guazatine-acetate, iminoctadine-triacetate, iminoctadine-tris(albesilate), nitrothal-isopropyl, mildiomycin, oxin-copper and prohexadione calcium. Very particularly preferred is metrafenone.

Particular preference is given to compositions of a compound 1) with a component 2) consisting of at least one active compound (II) selected from groups C), D) and F), whereas each of C), D) and F) may consist of all members or the preferred embodiments.

Preference is also given to three-component compositions comprising a component 1), wherein component 2) consists of two of the active compounds (II) mentioned above.

Preference is also given to three-component compositions comprising, in addition to component 1) and component 2) consisting of one active compound (II) mentioned above, a further fungicidally active compound V selected from active compound groups G) to M):

G) azoles selected from the group consisting of bitertanol, bromuconazole, cyproconazole, difenoconazole, diniconazole, enilconazole, epoxiconazole, fluquinconazole, fenbuconazole, flusilazole, flutriafol, hexaconazole, imibenconazole, ipconazole, metconazole, myclobutanil, penconazole, propiconazole, prothioconazole, simeconazole, triadimefon, triadimenol, tebuconazole, tetraconazole, triticonazole, prochloraz, pefurazoate, imazalil, triflumizole, cyazofamid, benomyl, carbendazim, thiabendazole, fuberidazole, ethaboxam, etridiazole and hymexazole;

H) strobilurins selected from the group consisting of azoxystrobin, dimoxystrobin, enestroburin, fluoxastrobin, kresoxim-methyl, methominostrobin, orysastrobin, picoxystrobin, pyraclostrobin, trifloxystrobin, enestroburin, methyl (2-chloro-5-[1-(3-methylbenzyloxyimino)ethyl]benzyl)carbamate, methyl (2-chloro-5-[1-(6-methylpyridin-2-ylmethoxyimino)ethyl]benzyl)carbamate and methyl 2-(ortho-(2,5-dimethylphenyloxymethylene)phenyl)-3-methoxyacrylate;

J) carboxamides selected from the group consisting of carboxin, boscalid, fenhexamid, flutolanil, furametpyr, mepronil, metalaxyl, mefenoxam, ofurace, oxadixyl, oxycarboxin, thifluzamide, tiadinil, 3,4-dichloro-N-(2-cyanophenyl)iso-thiazole-5-carboxamide, penthiopyrad, dimethomorph, flumorph, flumetover, fluopicolide (picobenzamid), zoxamide, carpropamid, diclocymet, mandipropamid, N-(2-(4-[3-(4-chlorophenyl) prop-2-ynyloxy]-3-ethoxyphenyl)ethyl)-2-methanesulfonylamino-3-methylbutyramide, N-(2-(4-[3-(4-chlorophenyl)prop-2-ynyloxy]-3-methoxyphenyl)ethyl)-2-ethanesulfonylamino-3-methylbutyramide, methyl 3-(4-chlorophenyl)-3-(2-isopropoxycarbonylamino-3-methylbutyrylamino)propionate, N-(4'-bromobiphenyl-2-yl)-4-difluoromethyl-2-methylthiazole-5-carboxamide, N-(4'-trifluoromethylbiphenyl-2-yl)-4-difluoromethyl-2-methylthiazole-5-carboxamide, N-(4'-chloro-3'-fluorobiphenyl-2-yl)-4-difluoromethyl-2-methyl-thiazole-5-carboxamide, N-(3',4'-dichloro-4-fluorobiphenyl-2-yl)-3-difluoromethyl-1-methylpyrazole-4-carboxamide and N-(2-cyanophenyl)-3,4-dichloroisothiazole-5-carboxamide;

K) heterocyclic compounds selected from the group consisting of fluazinam, pyrifenox, bupirimate, cyprodinil, fenarimol, ferimzone, mepanipyrim, nuarimol, pyrimethanil, triforine, fenpiclonil, fludioxonil, aldimorph, dodemorph, fenpropimorph, tridemorph, fenpropidin, iprodione, procymidone, vinclozolin, famoxadone, fenamidone, octhilinone, probenazole, 5-chloro-7-(4-methylpiperidin-1-yl)-6-(2,4,6-trifluorophenyl)-[1,2,4]triazolo[1,5-a]pyrimidine, anilazine, diclomezine, pyroquilon, proquinazid, tricyclazole, 2-butoxy-6-iodo-3-propylchromen-4-one, acibenzolar-S-methyl, captafol, captan, dazomet, folpet, fenoxanil, quinoxyfen and N,N-dimethyl-3-(3-bromo-6-fluoro-2-methylindole-1-sulfonyl)-[1,2,4]triazole-1-sulfonamide;

L) carbamates selected from the group consisting of mancozeb, maneb, metam, metiram, ferbam, propineb, thiram, zineb, ziram, diethofencarb, iprovalicarb, flubenthiavalicarb, propamocarb, 4-fluorophenyl N-(1-(1-(4-cyanophenyl)ethanesulfonyl)but-2-yl)carbamate, methyl 3-(4-chlorophenyl)-3-(2-isopropoxycarbonylamino-3-methylbutyrylamino)propanoate and carbamate oxime ethers of the formula VI

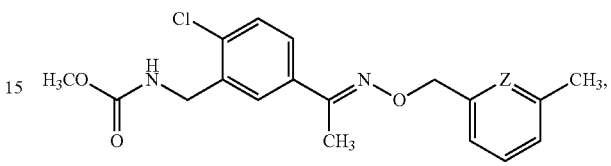

in which Z is N or CH;

M) other fungicides selected from the group consisting of guanidine, dodine, iminoctadine, guazatine, antibiotics: kasugamycin, streptomycin, polyoxin, validamycin A, nitrophenyl derivatives: binapacryl, dinocap, dinobuton, sulfur-containing heterocyclyl compounds: dithianon, isoprothiolane, organometallic compounds: fentin salts such as fentin acetate, organophosphorus compounds: edifenphos, iprobenfos, fosetyl, fosetyl-aluminum, phosphorous acid and its salts, pyrazophos, tolclofos-methyl, organochlorine compounds: chlorothalonil, dichlofluanid, flusulfamide, hexachlorbenzene, phthalide, pencycuron, quintozene, thiophanate-methyl, tolylfluanid, inorganic active compounds: Bordeaux mixture, copper acetate, copper hydroxide, copper oxychloride, basic copper sulfate, sulfur, others: cyflufenamid, cymoxanil, dimethirimol, ethirimol, furalaxyl and spiroxamine.

The active compounds V mentioned above, their preparation and their action against harmful fungi are generally known (cf., for example, http://www.hdrss.demon.co.uk/index.html); they are commercially available.

Preference is given to three-component compositions of components 1) and 2) with an active compound V selected from the group of the azoles G).

Preference is also given to three-component compositions of components 1) and 2) with an active compound V selected from the group of the strobilurins H).

Preference is given to three-component compositions of components 1) and 2) with an active compound V selected from the group of the carboxamides J).

Preference is furthermore also given to three-component compositions of components 1) and 2) with an active compound V selected from the group of the heterocyclic compounds K).

Preference is furthermore also given to three-component compositions of components 1) and 2) with an active compound V selected from the group of the carbamates L).

Preference is furthermore also given to three-component compositions of components 1) and 2) with an active compound selected from the group of the other fungicides M).

Preference is furthermore also given to three-component compositions of components 1) and 2) with an active compound selected from the group of the azoles G) selected from the group consisting of cyproconazole, difenoconazole, epoxiconazole, fluquinconazole, flusilazole, flutriafol, metconazole, myclobutanil, penconazole, propiconazole, prothioconazole, triadimefon, triadimenol, tebuconazole, tetraconazole, triticonazole, prochloraz, cyazofamid, benomyl, carbendazim and ethaboxam.

Particular preference is also given to three-component compositions of components 1) and 2) with an active compound selected from the group of the azoles G) selected from the group consisting of cyproconazole, difenoconazole, epoxiconazole, fluquinconazole, flusilazole, flutriafol, metconazole, myclobutanil, propiconazole, prothioconazole, triadimefon, triadimenol, tebuconazole, tetraconazole, triticonazole, prochloraz, cyazofamid, benomyl and carbendazim.

Very particular preference is also given to three-component compositions of components 1) and 2) with an active compound selected from the group of the azoles G) selected from the group consisting of epoxiconazole, fluquinconazole, flutriafol, metconazole, tebuconazole, triticonazole, prochloraz and carbendazim.

Preference is also given to three-component compositions of components 1) and 2) with at least one active compound selected from the group of the strobilurins H) selected from the group consisting of azoxystrobin, dimoxystrobin, fluoxastrobin, kresoxim-methyl, orysastrobin, picoxystrobin, pyraclostrobin and trifloxystrobin.

Particular preference is also given to three-component compositions of components 1) and 2) with an active compound selected from the group of the strobilurins H) selected from the group consisting of kresoxim-methyl, orysastrobin and pyraclostrobin.

Very particular preference is also given to three-component compositions of components 1) and 2) with pyraclostrobin.

Preference is also given to three-component compositions of components 1) and 2) with an active compound selected from the group of the carboxamides J) selected from the group consisting of fenhexamid, mefenoxam, ofurace, dimethomorph, flumorph, fluopicolide (picobenzamid), zoxamide, carpropamid and mandipropamid.

Particular preference is also given to three-component compositions of components 1) and 2) with an active compound selected from the group of the carboxamides J) selected from the group consisting of fenhexamid, metalaxyl, mefenoxam, ofurace, dimethomorph, zoxamide and carpropamid.

Preference is also given to three-component compositions of components 1) and 2) with an active compound selected from the group of the heterocyclic compounds J) selected from the group consisting of fluazinam, cyprodinil, fenarimol, mepanipyrim, pyrimethanil, triforine, fludioxonil, dodemorph, fenpropimorph, tridemorph, fenpropidin, iprodione, vinclozolin, famoxadone, fenamidone, probenazole, proquinazid, acibenzolar-S-methyl, captafol, folpet, fenoxanil and quinoxyfen, in particular fluazinam, cyprodinil, fenarimol, mepanipyrim, pyrimethanil, triforine, fludioxonil, dodemorph, fenpropimorph, tridemorph, fenpropidin, iprodione, vinclozolin, famoxadone, fenamidone, probenazole, proquinazid, acibenzolar-S-methyl, captafol, folpet, fenoxanil and quinoxyfen.

Particular preference is also given to three-component compositions of components 1) and 2) with an active compound selected from the group of the heterocyclic compounds K) selected from the group consisting of pyrimethanil, dodemorph, fenpropimorph, tridemorph, iprodione, vinclozolin and quinoxyfen, in particular pyrimethanil, dodemorph, fenpropimorph, tridemorph, iprodione, vinclozolin and quinoxyfen.

Preference is also given to three-component compositions of components 1) and 2) with at least one active compound selected from the group of the carbamates L) selected from the group consisting of mancozeb, metiram, propineb, thiram, iprovalicarb, flubenthiavalicarb and propamocarb.

Particular preference is also given to three-component compositions of components 1) and 2) with an active compound selected from the group of the carbamates L) selected from the group consisting of mancozeb and metiram.

Preference is also given to three-component compositions of components 1) and 2) with an active compound selected from the group of the other fungicides M) selected from the group consisting of dithianon, fentin salts, such as fentin acetate, fosetyl, fosetyl-aluminum, phosphorous acid and its salts, chlorothalonil, dichlofluanid, thiophanate-methyl, copper acetate, copper hydroxide, copper oxychloride, basic copper sulfate, sulfur, cymoxanil and spiroxamine.

Particular preference is also given to three-component compositions of components 1) and 2) with an active compound selected from the group of the other fungicides M) selected from the group consisting of phosphorous acid and its salts and chlorothalonil.

Preference is also given to four-component compositions of components 1) and 2) with two further active compounds selected from compounds II and V mentioned above.

Preferred active compound combinations are listed in tables 2 to 7 below:

TABLE 2

Active compound combinations of a component 1) and a component 2), comprising a compound II selected from group A):

| Mixture | Component 1) | Component 2) |
| --- | --- | --- |
| No. A.1 | RHAPSODY ® | azaconazole |
| No. A.2 | SERENADE ® MAX | azaconazole |
| No. A.3 | SERENADE ® ASO | azaconazole |
| No. A.4 | SONATA ® | azaconazole |
| No. A.5 | BALLAD ® Plus | azaconazole |
| No. A.6 | RHAPSODY ® | diniconazole-M |
| No. A.7 | SERENADE ® MAX | diniconazole-M |
| No. A.8 | SERENADE ® ASO | diniconazole-M |
| No. A.9 | SONATA ® | diniconazole-M |
| No. A.10 | BALLAD ® Plus | diniconazole-M |
| No. A.11 | RHAPSODY ® | oxpoconazol |
| No. A.12 | SERENADE ® MAX | oxpoconazol |
| No. A.13 | SERENADE ® ASO | oxpoconazol |
| No. A.14 | SONATA ® | oxpoconazol |
| No. A.15 | BALLAD ® Plus | oxpoconazol |
| No. A.16 | RHAPSODY ® | paclobutrazol |
| No. A.17 | SERENADE ® MAX | paclobutrazol |
| No. A.18 | SERENADE ® ASO | paclobutrazol |
| No. A.19 | SONATA ® | paclobutrazol |
| No. A.20 | BALLAD ® Plus | paclobutrazol |
| No. A.21 | RHAPSODY ® | uniconazol |
| No. A.22 | SERENADE ® MAX | uniconazol |
| No. A.23 | SERENADE ® ASO | uniconazol |
| No. A.24 | SONATA ® | uniconazol |
| No. A.25 | BALLAD ® Plus | uniconazol |
| No. A.26 | RHAPSODY ® | 1-(4-chloro-phenyl)-2-([1,2,4]triazol-1-yl)-cycloheptanol |
| No. A.27 | SERENADE ® MAX | 1-(4-chloro-phenyl)-2-([1,2,4]triazol-1-yl)-cycloheptanol |
| No. A.28 | SERENADE ® ASO | 1-(4-chloro-phenyl)-2-([1,2,4]triazol-1-yl)-cycloheptanol |
| No. A.29 | SONATA ® | 1-(4-chloro-phenyl)-2-([1,2,4]triazol-1-yl)-cycloheptanol |
| No. A.30 | BALLAD ® Plus | 1-(4-chloro-phenyl)-2-([1,2,4]triazol-1-yl)-cycloheptanol |
| No. A.31 | RHAPSODY ® | imazalil-sulfphate |
| No. A.32 | SERENADE ® MAX | imazalil-sulfphate |
| No. A.33 | SERENADE ® ASO | imazalil-sulfphate |
| No. A.34 | SONATA ® | imazalil-sulfphate |
| No. A.35 | BALLAD ® Plus | imazalil-sulfphate |

TABLE 3

Active compound combinations of a component 1) and a component 2), conprising a compound II selected from group B):

| Mixture | Component 1) | Component 2) |
| --- | --- | --- |
| No. B.1 | RHAPSODY ® | 2-(2-(6-(3-chloro-2-methyl-phenoxy)-5-fluoro-pyrimidin-4-yloxy)-phenyl)-2-methoxyimino-N-methyl-acetamide |
| No. B.2 | SERENADE ® MAX | 2-(2-(6-(3-chloro-2-methyl-phenoxy)-5-fluoro-pyrimidin-4-yloxy)-phenyl)-2-methoxyimino-N-methyl-acetamide |
| No. B.2 | SERENADE ® ASO | 2-(2-(6-(3-chloro-2-methyl-phenoxy)-5-fluoro-pyrimidin-4-yloxy)-phenyl)-2-methoxyimino-N-methyl-acetamide |
| No. B.1 | SONATA ® | 2-(2-(6-(3-chloro-2-methyl-phenoxy)-5-fluoro-pyrimidin-4-yloxy)-phenyl)-2-methoxyimino-N-methyl-acetamide |
| No. B.2 | BALLAD ® Plus | 2-(2-(6-(3-chloro-2-methyl-phenoxy)-5-fluoro-pyrimidin-4-yloxy)-phenyl)-2-methoxyimino-N-methyl-acetamide |
| No. B.3 | RHAPSODY ® | 3-methoxy-2-(2-(N-(4-methoxy-phenyl)-cyclopropanecarboximidoylsulfanylmethyl)-phenyl)-acrylic acid methyl ester |
| No. B.4 | SERENADE ® MAX | 3-methoxy-2-(2-(N-(4-methoxy-phenyl)-cyclopropanecarboximidoylsulfanylmethyl)-phenyl)-acrylic acid methyl ester |
| No. B.3 | SERENADE ® ASO | 3-methoxy-2-(2-(N-(4-methoxy-phenyl)-cyclopropanecarboximidoylsulfanylmethyl)-phenyl)-acrylic acid methyl ester |
| No. B.3 | SONATA ® | 3-methoxy-2-(2-(N-(4-methoxy-phenyl)-cyclopropanecarboximidoylsulfanylmethyl)-phenyl)-acrylic acid methyl ester |
| No. B.4 | BALLAD ® Plus | 3-methoxy-2-(2-(N-(4-methoxy-phenyl)-cyclopropanecarboximidoylsulfanylmethyl)-phenyl)-acrylic acid methyl ester |

TABLE 4

Active compound combinations of a component 1) and a component 2), conprising a compound II selected from group C):

| Mixture | Component 1) | Component 2) |
| --- | --- | --- |
| No. C.1 | RHAPSODY ® | benalaxyl-M |
| No. C.2 | SERENADE ® MAX | benalaxyl-M |
| No. C.3 | SERENADE ® ASO | benalaxyl-M |
| No. C.4 | SONATA ® | benalaxyl-M |
| No. C.5 | BALLAD ® Plus | benalaxyl-M |
| No. C.6 | RHAPSODY ® | 2-amino-4-methyl-thiazole-5-carboxanilide |
| No. C.7 | SERENADE ® MAX | 2-amino-4-methyl-thiazole-5-carboxanilide |
| No. C.8 | SERENADE ® ASO | 2-amino-4-methyl-thiazole-5-carboxanilide |
| No. C.9 | SONATA ® | 2-amino-4-methyl-thiazole-5-carboxanilide |
| No. C.10 | BALLAD ® Plus | 2-amino-4-methyl-thiazole-5-carboxanilide |
| No. C.11 | RHAPSODY ® | 2-chloro-N-(1,1,3-trimethyl-indan-4-yl)-nicotinamide |
| No. C.12 | SERENADE ® MAX | 2-chloro-N-(1,1,3-trimethyl-indan-4-yl)-nicotinamide |
| No. C.13 | SERENADE ® ASO | 2-chloro-N-(1,1,3-trimethyl-indan-4-yl)-nicotinamide |
| No. C.14 | SONATA ® | 2-chloro-N-(1,1,3-trimethyl-indan-4-yl)-nicotinamide |
| No. C.15 | BALLAD ® Plus | 2-chloro-N-(1,1,3-trimethyl-indan-4-yl)-nicotinamide |
| No. C.16 | RHAPSODY ® | N-(2-(1,3-dimethylbutyl)-phenyl)-1,3-dimethyl-5-fluoro-1H-pyrazole-4-carboxamide |
| No. C.17 | SERENADE ® MAX | N-(2-(1,3-dimethylbutyl)-phenyl)-1,3-dimethyl-5-fluoro-1H-pyrazole-4-carboxamide |
| No. C.18 | SERENADE ® ASO | N-(2-(1,3-dimethylbutyl)-phenyl)-1,3-dimethyl-5-fluoro-1H-pyrazole-4-carboxamide |
| No. C.19 | SONATA ® | N-(2-(1,3-dimethylbutyl)-phenyl)-1,3-dimethyl-5-fluoro-1H-pyrazole-4-carboxamide |
| No. C.20 | BALLAD ® Plus | N-(2-(1,3-dimethylbutyl)-phenyl)-1,3-dimethyl-5-fluoro-1H-pyrazole-4-carboxamide |
| No. C.21 | RHAPSODY ® | N-(4'-chloro-3',5-difluoro-biphenyl-2-yl)-3-difluoromethyl-1-methyl-1H-pyrazole-4-carboxamide |
| No. C.22 | SERENADE ® MAX | N-(4'-chloro-3',5-difluoro-biphenyl-2-yl)-3-difluoromethyl-1-methyl-1H-pyrazole-4-carboxamide |
| No. C.23 | SERENADE ® ASO | N-(4'-chloro-3',5-difluoro-biphenyl-2-yl)-3-difluoromethyl-1-methyl-1H-pyrazole-4-carboxamide |
| No. C.24 | SONATA ® | N-(4'-chloro-3',5-difluoro-biphenyl-2-yl)-3-difluoromethyl-1-methyl-1H-pyrazole-4-carboxamide |
| No. C.25 | BALLAD ® Plus | N-(4'-chloro-3',5-difluoro-biphenyl-2-yl)-3-difluoromethyl-1-methyl-1H-pyrazole-4-carboxamide |
| No. C.26 | RHAPSODY ® | N-(4'-chloro-3',5-difluoro-biphenyl-2-yl)-3-trifluoromethyl-1-methyl-1H-pyrazole-4-carboxamide |
| No. C.27 | SERENADE ® MAX | N-(4'-chloro-3',5-difluoro-biphenyl-2-yl)-3-trifluoromethyl-1-methyl-1H-pyrazole-4-carboxamide |
| No. C.28 | SERENADE ® ASO | N-(4'-chloro-3',5-difluoro-biphenyl-2-yl)-3-trifluoromethyl-1-methyl-1H-pyrazole-4-carboxamide |
| No. C.29 | SONATA ® | N-(4'-chloro-3',5-difluoro-biphenyl-2-yl)-3-trifluoromethyl-1-methyl-1H-pyrazole-4-carboxamide |

TABLE 4-continued

Active compound combinations of a component 1) and a component 2), comprising a compound II selected from group C):

| Mixture | Component 1) | Component 2) |
|---|---|---|
| No. C.30 | BALLAD ® Plus | N-(4'-chloro-3',5-difluoro-biphenyl-2-yl)-3-trifluoromethyl-1-methyl-1H-pyrazole-4-carboxamide |
| No. C.31 | RHAPSODY ® | N-(3',4'-dichloro-5-fluoro-biphenyl-2-yl)-3-difluoromethyl-1-methyl-1H-pyrazole-4-carboxamide |
| No. C.32 | SERENADE ® MAX | N-(3',4'-dichloro-5-fluoro-biphenyl-2-yl)-3-difluoromethyl-1-methyl-1H-pyrazole-4-carboxamide |
| No. C.33 | SERENADE ® ASO | N-(3',4'-dichloro-5-fluoro-biphenyl-2-yl)-3-difluoromethyl-1-methyl-1H-pyrazole-4-carboxamide |
| No. C.34 | SONATA ® | N-(3',4'-dichloro-5-fluoro-biphenyl-2-yl)-3-difluoromethyl-1-methyl-1H-pyrazole-4-carboxamide |
| No. C.35 | BALLAD ® Plus | N-(3',4'-dichloro-5-fluoro-biphenyl-2-yl)-3-difluoromethyl-1-methyl-1H-pyrazole-4-carboxamide |
| No. C.36 | RHAPSODY ® | N-(3',5-difluoro-4'-methyl-biphenyl-2-yl)-3-difluoromethyl-1-methyl-1H-pyrazole-4-carboxamide |
| No. C.37 | SERENADE ® MAX | N-(3',5-difluoro-4'-methyl-biphenyl-2-yl)-3-difluoromethyl-1-methyl-1H-pyrazole-4-carboxamide |
| No. C.38 | SERENADE ® ASO | N-(3',5-difluoro-4'-methyl-biphenyl-2-yl)-3-difluoromethyl-1-methyl-1H-pyrazole-4-carboxamide |
| No. C.39 | SONATA ® | N-(3',5-difluoro-4'-methyl-biphenyl-2-yl)-3-difluoromethyl-1-methyl-1H-pyrazole-4-carboxamide |
| No. C.40 | BALLAD ® Plus | N-(3',5-difluoro-4'-methyl-biphenyl-2-yl)-3-difluoromethyl-1-methyl-1H-pyrazole-4-carboxamide |
| No. C.41 | RHAPSODY ® | N-(3',5-difluoro-4'-methyl-biphenyl-2-yl)-3-trifluoromethyl-1-methyl-1H-pyrazole-4-carboxamide |
| No. C.42 | SERENADE ® MAX | N-(3',5-difluoro-4'-methyl-biphenyl-2-yl)-3-trifluoromethyl-1-methyl-1H-pyrazole-4-carboxamide |
| No. C.43 | SERENADE ® ASO | N-(3',5-difluoro-4'-methyl-biphenyl-2-yl)-3-trifluoromethyl-1-methyl-1H-pyrazole-4-carboxamide |
| No. C.44 | SONATA ® | N-(3',5-difluoro-4'-methyl-biphenyl-2-yl)-3-trifluoromethyl-1-methyl-1H-pyrazole-4-carboxamide |
| No. C.45 | BALLAD ® Plus | N-(3',5-difluoro-4'-methyl-biphenyl-2-yl)-3-trifluoromethyl-1-methyl-1H-pyrazole-4-carboxamide |
| No. C.46 | RHAPSODY ® | N-(cis-2-bicyclopropyl-2-yl-phenyl)-3-difluoromethyl-1-methyl-1H-pyrazole-4-carboxamide |
| No. C.47 | SERENADE ® MAX | N-(cis-2-bicyclopropyl-2-yl-phenyl)-3-difluoromethyl-1-methyl-1H-pyrazole-4-carboxamide |
| No. C.48 | SERENADE ® ASO | N-(cis-2-bicyclopropyl-2-yl-phenyl)-3-difluoromethyl-1-methyl-1H-pyrazole-4-carboxamide |
| No. C.49 | SONATA ® | N-(cis-2-bicyclopropyl-2-yl-phenyl)-3-difluoromethyl-1-methyl-1H-pyrazole-4-carboxamide |
| No. C.50 | BALLAD ® Plus | N-(cis-2-bicyclopropyl-2-yl-phenyl)-3-difluoromethyl-1-methyl-1H-pyrazole-4-carboxamide |
| No. C.51 | RHAPSODY ® | N-(trans-2-bicyclopropyl-2-yl-phenyl)-3-difluoromethyl-1-methyl-1H-pyrazole-4-carboxamide |
| No. C.52 | SERENADE ® MAX | N-(trans-2-bicyclopropyl-2-yl-phenyl)-3-difluoromethyl-1-methyl-1H-pyrazole-4-carboxamide |
| No. C.53 | SERENADE ® ASO | N-(trans-2-bicyclopropyl-2-yl-phenyl)-3-difluoromethyl-1-methyl-1H-pyrazole-4-carboxamide |
| No. C.54 | SONATA ® | N-(trans-2-bicyclopropyl-2-yl-phenyl)-3-difluoromethyl-1-methyl-1H-pyrazole-4-carboxamide |
| No. C.55 | BALLAD ® Plus | N-(trans-2-bicyclopropyl-2-yl-phenyl)-3-difluoromethyl-1-methyl-1H-pyrazole-4-carboxamide |
| No. C.56 | RHAPSODY ® | fluopyram |
| No. C.57 | SERENADE ® MAX | fluopyram |
| No. C.58 | SERENADE ® ASO | fluopyram |
| No. C.59 | SONATA ® | fluopyram |
| No. C.60 | BALLAD ® Plus | fluopyram |
| No. C.61 | RHAPSODY ® | N-(3-ethyl-3,5-5-trimethyl-cyclohexyl)-3-formylamino-2-hydroxy-benzamide |
| No. C.62 | SERENADE ® MAX | N-(3-ethyl-3,5-5-trimethyl-cyclohexyl)-3-formylamino-2-hydroxy-benzamide |
| No. C.63 | SERENADE ® ASO | N-(3-ethyl-3,5-5-trimethyl-cyclohexyl)-3-formylamino-2-hydroxy-benzamide |
| No. C.64 | SONATA ® | N-(3-ethyl-3,5-5-trimethyl-cyclohexyl)-3-formylamino-2-hydroxy-benzamide |
| No. C.65 | BALLAD ® Plus | N-(3-ethyl-3,5-5-trimethyl-cyclohexyl)-3-formylamino-2-hydroxy-benzamide |
| No. C.66 | RHAPSODY ® | oxytetracyclin |
| No. C.67 | SERENADE ® MAX | oxytetracyclin |
| No. C.68 | SERENADE ® ASO | oxytetracyclin |
| No. C.69 | SONATA ® | oxytetracyclin |
| No. C.70 | BALLAD ® Plus | oxytetracyclin |
| No. C.71 | RHAPSODY ® | silthiofam |
| No. C.72 | SERENADE ® MAX | silthiofam |
| No. C.73 | SERENADE ® ASO | silthiofam |

TABLE 4-continued

Active compound combinations of a component 1) and a component 2), comprising a compound II selected from group C):

| Mixture | Component 1) | Component 2) |
|---|---|---|
| No. C.74 | SONATA ® | silthiofam |
| No. C.75 | BALLAD ® Plus | silthiofam |
| No. C.76 | RHAPSODY ® | N-(6-methoxy-pyridin-3-yl) cyclopropanecarboxamide |
| No. C.77 | SERENADE ® MAX | N-(6-methoxy-pyridin-3-yl) cyclopropanecarboxamide |
| No. C.78 | SERENADE ® ASO | N-(6-methoxy-pyridin-3-yl) cyclopropanecarboxamide |
| No. C.79 | SONATA ® | N-(6-methoxy-pyridin-3-yl) cyclopropanecarboxamide |
| No. C.80 | BALLAD ® Plus | N-(6-methoxy-pyridin-3-yl) cyclopropanecarboxamide |
| No. C.81 | RHAPSODY ® | N-(2'-fluoro-4'-chloro-5'-methylbiphenyl-2-yl)-1-methyl-3-trifluoromethyl-1H-pyrazole-4-carboxamide |
| No. C.82 | SERENADE ® MAX | N-(2'-fluoro-4'-chloro-5'-methylbiphenyl-2-yl)-1-methyl-3-trifluoromethyl-1H-pyrazole-4-carboxamide |
| No. C.83 | SERENADE ® ASO | N-(2'-fluoro-4'-chloro-5'-methylbiphenyl-2-yl)-1-methyl-3-trifluoromethyl-1H-pyrazole-4-carboxamide |
| No. C.84 | SONATA ® | N-(2'-fluoro-4'-chloro-5'-methylbiphenyl-2-yl)-1-methyl-3-trifluoromethyl-1H-pyrazole-4-carboxamide |
| No. C.85 | BALLAD ® Plus | N-(2'-fluoro-4'-chloro-5'-methylbiphenyl-2-yl)-1-methyl-3-trifluoromethyl-1H-pyrazole-4-carboxamide |
| No. C.86 | RHAPSODY ® | N-(3',4',5'-trifluorobiphenyl-2-yl)-1-methyl-3-trifluoromethyl-1H-pyrazole-4-carboxamide |
| No. C.87 | SERENADE ® MAX | N-(3',4',5'-trifluorobiphenyl-2-yl)-1-methyl-3-trifluoromethyl-1H-pyrazole-4-carboxamide |
| No. C.88 | SERENADE ® ASO | N-(3',4',5'-trifluorobiphenyl-2-yl)-1-methyl-3-trifluoromethyl-1H-pyrazole-4-carboxamide |
| No. C.89 | SONATA ® | N-(3',4',5'-trifluorobiphenyl-2-yl)-1-methyl-3-trifluoromethyl-1H-pyrazole-4-carboxamide |
| No. C.90 | BALLAD ® Plus | N-(3',4',5'-trifluorobiphenyl-2-yl)-1-methyl-3-trifluoromethyl-1H-pyrazole-4-carboxamide |
| No. C.91 | RHAPSODY ® | N-(3',4',5'-trifluorobiphenyl-2-yl)-1-methyl-3-difluoromethyl-1H-pyrazole-4-carboxamide |
| No. C.92 | SERENADE ® MAX | N-(3',4',5'-trifluorobiphenyl-2-yl)-1-methyl-3-difluoromethyl-1H-pyrazole-4-carboxamide |
| No. C.93 | SERENADE ® ASO | N-(3',4',5'-trifluorobiphenyl-2-yl)-1-methyl-3-difluoromethyl-1H-pyrazole-4-carboxamide |
| No. C.94 | SONATA ® | N-(3',4',5'-trifluorobiphenyl-2-yl)-1-methyl-3-difluoromethyl-1H-pyrazole-4-carboxamide |
| No. C.95 | BALLAD ® Plus | N-(3',4',5'-trifluorobiphenyl-2-yl)-1-methyl-3-difluoromethyl-1H-pyrazole-4-carboxamide |
| No. C.96 | RHAPSODY ® | N-(2',4',5'-trifluorobiphenyl-2-yl)-1-methyl-3-difluoromethyl-1H-pyrazole-4-carboxamide |
| No. C.97 | SERENADE ® MAX | N-(2',4',5'-trifluorobiphenyl-2-yl)-1-methyl-3-difluoromethyl-1H-pyrazole-4-carboxamide |
| No. C.98 | SERENADE ® ASO | N-(2',4',5'-trifluorobiphenyl-2-yl)-1-methyl-3-difluoromethyl-1H-pyrazole-4-carboxamide |
| No. C.99 | SONATA ® | N-(2',4',5'-trifluorobiphenyl-2-yl)-1-methyl-3-difluoromethyl-1H-pyrazole-4-carboxamide |
| No. C.100 | BALLAD ® Plus | N-(2',4',5'-trifluorobiphenyl-2-yl)-1-methyl-3-difluoromethyl-1H-pyrazole-4-carboxamide |
| No. C.101 | RHAPSODY ® | N-(3',4',5'-trifluorobiphenyl-2-yl)-3-chlorofluoromethyl-1-methyl-1H-pyrazole-4-carboxamide |
| No. C.102 | SERENADE ® MAX | N-(3',4',5'-trifluorobiphenyl-2-yl)-3-chlorofluoromethyl-1-methyl-1H-pyrazole-4-carboxamide |
| No. C.103 | SERENADE ® ASO | N-(3',4',5'-trifluorobiphenyl-2-yl)-3-chlorofluoromethyl-1-methyl-1H-pyrazole-4-carboxamide |
| No. C.104 | SONATA ® | N-(3',4',5'-trifluorobiphenyl-2-yl)-3-chlorofluoromethyl-1-methyl-1H-pyrazole-4-carboxamide |
| No. C.105 | BALLAD ® Plus | N-(3',4',5'-trifluorobiphenyl-2-yl)-3-chlorofluoromethyl-1-methyl-1H-pyrazole-4-carboxamide |
| No. C.106 | RHAPSODY ® | N-(4'-trifluoromethylthio-biphenyl-2-yl)-3-difluoro-methyl-1-methyl-1H-pyrazole-4-carboxamide |
| No. C.107 | SERENADE ® MAX | N-(4'-trifluoromethylthio-biphenyl-2-yl)-3-difluoro-methyl-1-methyl-1H-pyrazole-4-carboxamide |
| No. C.108 | SERENADE ® ASO | N-(4'-trifluoromethylthio-biphenyl-2-yl)-3-difluoro-methyl-1-methyl-1H-pyrazole-4-carboxamide |
| No. C.109 | SONATA ® | N-(4'-trifluoromethylthio-biphenyl-2-yl)-3-difluoro-methyl-1-methyl-1H-pyrazole-4-carboxamide |
| No. C.110 | BALLAD ® Plus | N-(4'-trifluoromethylthio-biphenyl-2-yl)-3-difluoro-methyl-1-methyl-1H-pyrazole-4-carboxamide |
| No. C.111 | RHAPSODY ® | N-(4'-trifluoromethylthio-biphenyl-2-yl)-1-methyl-3-trfluoromethyl-1H-pyrazole-4-carboxamide |
| No. C.112 | SERENADE ® MAX | N-(4'-trifluoromethylthio-biphenyl-2-yl)-1-methyl-3-trfluoromethyl-1H-pyrazole-4-carboxamide |
| No. C.113 | SERENADE ® ASO | N-(4'-trifluoromethylthio-biphenyl-2-yl)-1-methyl-3-trfluoromethyl-1H-pyrazole-4-carboxamide |
| No. C.114 | SONATA ® | N-(4'-trifluoromethylthio-biphenyl-2-yl)-1-methyl-3-trfluoromethyl-1H-pyrazole-4-carboxamide |

TABLE 4-continued

Active compound combinations of a component 1) and a component 2), conprising a compound II selected from group C):

| Mixture | Component 1) | Component 2) |
|---|---|---|
| No. C.115 | BALLAD ® Plus | N-(4'-trifluoromethylthio-biphenyl-2-yl)-1-methyl-3-trfluoromethyl-1H-pyrazole-4-carboxamide |
| No. C.116 | RHAPSODY ® | isopyrazam |
| No. C.117 | SERENADE ® MAX | isopyrazam |
| No. C.118 | SERENADE ® ASO | isopyrazam |
| No. C.119 | SONATA ® | isopyrazam |
| No. C.120 | BALLAD ® Plus | isopyrazam |

TABLE 5

Active compound combinations of a component 1) and a component 2), conprising a compound II selected from group D):

| Mixture | Component 1) | Component 2) |
|---|---|---|
| No. D.1 | RHAPSODY ® | 2,3,5,6-tetrachloro-4-methanesulfonyl-pyridine |
| No. D.2 | SERENADE ® MAX | 2,3,5,6-tetrachloro-4-methanesulfonyl-pyridine |
| No. D.3 | SERENADE ® ASO | 2,3,5,6-tetrachloro-4-methanesulfonyl-pyridine |
| No. D.4 | SONATA ® | 2,3,5,6-tetrachloro-4-methanesulfonyl-pyridine |
| No. D.5 | BALLAD ® Plus | 2,3,5,6-tetrachloro-4-methanesulfonyl-pyridine |
| No. D.6 | RHAPSODY ® | 3,4,5-trichloro-pyridine-2,6-di-carbonitrile |
| No. D.7 | SERENADE ® MAX | 3,4,5-trichloro-pyridine-2,6-di-carbonitrile |
| No. D.8 | SERENADE ® ASO | 3,4,5-trichloro-pyridine-2,6-di-carbonitrile |
| No. D.9 | SONATA ® | 3,4,5-trichloro-pyridine-2,6-di-carbonitrile |
| No. D.10 | BALLAD ® Plus | 3,4,5-trichloro-pyridine-2,6-di-carbonitrile |
| No. D.11 | RHAPSODY ® | N-(1-(5-bromo-3-chloro-pyridin-2-yl)-ethyl)-2,4-dichloro-nicotinamide |
| No. D.12 | SERENADE ® MAX | N-(1-(5-bromo-3-chloro-pyridin-2-yl)-ethyl)-2,4-dichloro-nicotinamide |
| No. D.13 | SERENADE ® ASO | N-(1-(5-bromo-3-chloro-pyridin-2-yl)-ethyl)-2,4-dichloro-nicotinamide |
| No. D.14 | SONATA ® | N-(1-(5-bromo-3-chloro-pyridin-2-yl)-ethyl)-2,4-dichloro-nicotinamide |
| No. D.15 | BALLAD ® Plus | N-(1-(5-bromo-3-chloro-pyridin-2-yl)-ethyl)-2,4-dichloro-nicotinamide |
| No. D.16 | RHAPSODY ® | N-((5-bromo-3-chloro-pyridin-2-yl)-methyl)-2,4-dichloro-nicotinamide |
| No. D.17 | SERENADE ® MAX | N-((5-bromo-3-chloro-pyridin-2-yl)-methyl)-2,4-dichloro-nicotinamide |
| No. D.18 | SERENADE ® ASO | N-((5-bromo-3-chloro-pyridin-2-yl)-methyl)-2,4-dichloro-nicotinamide |
| No. D.19 | SONATA ® | N-((5-bromo-3-chloro-pyridin-2-yl)-methyl)-2,4-dichloro-nicotinamide |
| No. D.20 | BALLAD ® Plus | N-((5-bromo-3-chloro-pyridin-2-yl)-methyl)-2,4-dichloro-nicotinamide |
| No. D.21 | RHAPSODY ® | diflumetorim |
| No. D.22 | SERENADE ® MAX | diflumetorim |
| No. D.23 | SERENADE ® ASO | diflumetorim |
| No. D.24 | SONATA ® | diflumetorim |
| No. D.25 | BALLAD ® Plus | diflumetorim |
| No. D.26 | RHAPSODY ® | nitrapyrin |
| No. D.27 | SERENADE ® MAX | nitrapyrin |
| No. D.28 | SERENADE ® ASO | nitrapyrin |
| No. D.29 | SONATA ® | nitrapyrin |
| No. D.30 | BALLAD ® Plus | nitrapyrin |
| No. D.31 | RHAPSODY ® | dodemorph-acetate |
| No. D.32 | SERENADE ® MAX | dodemorph-acetate |
| No. D.33 | SERENADE ® ASO | dodemorph-acetate |
| No. D.34 | SONATA ® | dodemorph-acetate |
| No. D.35 | BALLAD ® Plus | dodemorph-acetate |
| No. D.36 | RHAPSODY ® | fluoroimid |
| No. D.37 | SERENADE ® MAX | fluoroimid |
| No. D.38 | SERENADE ® ASO | fluoroimid |
| No. D.39 | SONATA ® | fluoroimid |
| No. D.40 | BALLAD ® Plus | fluoroimid |
| No. D.41 | RHAPSODY ® | blasticidin-S |
| No. D.42 | SERENADE ® MAX | blasticidin-S |
| No. D.43 | SERENADE ® ASO | blasticidin-S |
| No. D.44 | SONATA ® | blasticidin-S |
| No. D.45 | BALLAD ® Plus | blasticidin-S |
| No. D.46 | RHAPSODY ® | chinomethionat |
| No. D.47 | SERENADE ® MAX | chinomethionat |

TABLE 5-continued

Active compound combinations of a component 1) and a component 2), comprising a compound II selected from group D):

| Mixture | Component 1) | Component 2) |
|---|---|---|
| No. D.48 | SERENADE ® ASO | chinomethionat |
| No. D.49 | SONATA ® | chinomethionat |
| No. D.50 | BALLAD ® Plus | chinomethionat |
| No. D.51 | RHAPSODY ® | debacarb |
| No. D.52 | SERENADE ® MAX | debacarb |
| No. D.53 | SERENADE ® ASO | debacarb |
| No. D.54 | SONATA ® | debacarb |
| No. D.55 | BALLAD ® Plus | debacarb |
| No. D.56 | RHAPSODY ® | difenzoquat |
| No. D.57 | SERENADE ® MAX | difenzoquat |
| No. D.58 | SERENADE ® ASO | difenzoquat |
| No. D.59 | SONATA ® | difenzoquat |
| No. D.60 | BALLAD ® Plus | difenzoquat |
| No. D.61 | RHAPSODY ® | difenzoquat-methylsulphat |
| No. D.62 | SERENADE ® MAX | difenzoquat-methylsulphat |
| No. D.63 | SERENADE ® ASO | difenzoquat-methylsulphat |
| No. D.64 | SONATA ® | difenzoquat-methylsulphat |
| No. D.65 | BALLAD ® Plus | difenzoquat-methylsulphat |
| No. D.66 | RHAPSODY ® | oxolinic acid |
| No. D.67 | SERENADE ® MAX | oxolinic acid |
| No. D.68 | SERENADE ® ASO | oxolinic acid |
| No. D.69 | SONATA ® | oxolinic acid |
| No. D.70 | BALLAD ® Plus | oxolinic acid |
| No. D.71 | RHAPSODY ® | piperalin |
| No. D.72 | SERENADE ® MAX | piperalin |
| No. D.73 | SERENADE ® ASO | piperalin |
| No. D.74 | SONATA ® | piperalin |
| No. D.75 | BALLAD ® Plus | piperalin |
| No. D.76 | RHAPSODY ® | 5-chloro-7-(4-methylpiperidin-1-yl)-6-(2,4,6-trifluorophenyl)-[1,2,4]triazolo[1,5-a]pyrimidine |
| No. D.77 | SERENADE ® MAX | 5-chloro-7-(4-methylpiperidin-1-yl)-6-(2,4,6-trifluorophenyl)-[1,2,4]triazolo[1,5-a]pyrimidine |
| No. D.78 | SERENADE ® ASO | 5-chloro-7-(4-methylpiperidin-1-yl)-6-(2,4,6-trifluorophenyl)-[1,2,4]triazolo[1,5-a]pyrimidine |
| No. D.79 | SONATA ® | 5-chloro-7-(4-methylpiperidin-1-yl)-6-(2,4,6-trifluorophenyl)-[1,2,4]triazolo[1,5-a]pyrimidine |
| No. D.80 | BALLAD ® Plus | 5-chloro-7-(4-methylpiperidin-1-yl)-6-(2,4,6-trifluorophenyl)-[1,2,4]triazolo[1,5-a]pyrimidine |
| No. D.81 | RHAPSODY ® | 6-(3,4-dichlorophenyl)-5-methyl-[1,2,4]triazolo[1,5-a]pyrimidin-7-ylamine |
| No. D.82 | SERENADE ® MAX | 6-(3,4-dichlorophenyl)-5-methyl-[1,2,4]triazolo[1,5-a]pyrimidin-7-ylamine |
| No. D.83 | SERENADE ® ASO | 6-(3,4-dichlorophenyl)-5-methyl-[1,2,4]triazolo[1,5-a]pyrimidin-7-ylamine |
| No. D.84 | SONATA ® | 6-(3,4-dichlorophenyl)-5-methyl-[1,2,4]triazolo[1,5-a]pyrimidin-7-ylamine |
| No. D.85 | BALLAD ® Plus | 6-(3,4-dichlorophenyl)-5-methyl-[1,2,4]triazolo[1,5-a]pyrimidin-7-ylamine |
| No. D.86 | RHAPSODY ® | 6-(4-tert-butylphenyl)-5-methyl-[1,2,4]triazolo[1,5-a]pyrimidin-7-ylamine |
| No. D.87 | SERENADE ® MAX | 6-(4-tert-butylphenyl)-5-methyl-[1,2,4]triazolo[1,5-a]pyrimidin-7-ylamine |
| No. D.88 | SERENADE ® ASO | 6-(4-tert-butylphenyl)-5-methyl-[1,2,4]triazolo[1,5-a]pyrimidin-7-ylamine |
| No. D.89 | SONATA ® | 6-(4-tert-butylphenyl)-5-methyl-[1,2,4]triazolo[1,5-a]pyrimidin-7-ylamine |
| No. D.90 | BALLAD ® Plus | 6-(4-tert-butylphenyl)-5-methyl-[1,2,4]triazolo[1,5-a]pyrimidin-7-ylamine |
| No. D.91 | RHAPSODY ® | 5-methyl-6-(3,5,5-trimethylhexyl)-[1,2,4]triazolo[1,5-a]pyrimidin-7-ylamine |
| No. D.92 | SERENADE ® MAX | 5-methyl-6-(3,5,5-trimethylhexyl)-[1,2,4]triazolo[1,5-a]pyrimidin-7-ylamine |
| No. D.93 | SERENADE ® ASO | 5-methyl-6-(3,5,5-trimethylhexyl)-[1,2,4]triazolo[1,5-a]pyrimidin-7-ylamine |
| No. D.94 | SONATA ® | 5-methyl-6-(3,5,5-trimethylhexyl)-[1,2,4]triazolo[1,5-a]pyrimidin-7-ylamine |
| No. D.95 | BALLAD ® Plus | 5-methyl-6-(3,5,5-trimethylhexyl)-[1,2,4]triazolo[1,5-a]pyrimidin-7-ylamine |
| No. D.96 | RHAPSODY ® | 5-methyl-6-octyl-[1,2,4]triazolo[1,5-a]pyrimidin-7-ylamine |
| No. D.97 | SERENADE ® MAX | 5-methyl-6-octyl-[1,2,4]triazolo[1,5-a]pyrimidin-7-ylamine |
| No. D.98 | SERENADE ® ASO | 5-methyl-6-octyl-[1,2,4]triazolo[1,5-a]pyrimidin-7-ylamine |

TABLE 5-continued

Active compound combinations of a component 1) and a component 2), conprising a compound II selected from group D):

| Mixture | Component 1) | Component 2) |
|---|---|---|
| No. D.99 | SONATA ® | 5-methyl-6-octyl-[1,2,4]triazolo[1,5-a]pyrimidin-7-ylamine |
| No. D.100 | BALLAD ® Plus | 5-methyl-6-octyl-[1,2,4]triazolo[1,5-a]pyrimidin-7-ylamine |
| No. D.101 | RHAPSODY ® | 5-ethyl-6-octyl-[1,2,4]triazolo[1,5-a]pyrimidin-2,7-diamine |
| No. D.102 | SERENADE ® MAX | 5-ethyl-6-octyl-[1,2,4]triazolo[1,5-a]pyrimidin-2,7-diamine |
| No. D.103 | SERENADE ® ASO | 5-ethyl-6-octyl-[1,2,4]triazolo[1,5-a]pyrimidin-2,7-diamine |
| No. D.104 | SONATA ® | 5-ethyl-6-octyl-[1,2,4]triazolo[1,5-a]pyrimidin-2,7-diamine |
| No. D.105 | BALLAD ® Plus | 5-ethyl-6-octyl-[1,2,4]triazolo[1,5-a]pyrimidin-2,7-diamine |
| No. D.106 | RHAPSODY ® | 6-ethyl-5-octyl-[1,2,4]triazolo[1,5-a]pyrimidin-7-yl-amine |
| No. D.107 | SERENADE ® MAX | 6-ethyl-5-octyl-[1,2,4]triazolo[1,5-a]pyrimidin-7-yl-amine |
| No. D.108 | SERENADE ® ASO | 6-ethyl-5-octyl-[1,2,4]triazolo[1,5-a]pyrimidin-7-yl-amine |
| No. D.109 | SONATA ® | 6-ethyl-5-octyl-[1,2,4]triazolo[1,5-a]pyrimidin-7-yl-amine |
| No. D.110 | BALLAD ® Plus | 6-ethyl-5-octyl-[1,2,4]triazolo[1,5-a]pyrimidin-7-yl-amine |
| No. D.111 | RHAPSODY ® | 5-ethyl-6-octyl-[1,2,4]triazolo[1,5-a]pyrimidin-7-ylamine |
| No. D.112 | SERENADE ® MAX | 5-ethyl-6-octyl-[1,2,4]triazolo[1,5-a]pyrimidin-7-ylamine |
| No. D.113 | SERENADE ® ASO | 5-ethyl-6-octyl-[1,2,4]triazolo[1,5-a]pyrimidin-7-ylamine |
| No. D.114 | SONATA ® | 5-ethyl-6-octyl-[1,2,4]triazolo[1,5-a]pyrimidin-7-ylamine |
| No. D.115 | BALLAD ® Plus | 5-ethyl-6-octyl-[1,2,4]triazolo[1,5-a]pyrimidin-7-ylamine |
| No. D.116 | RHAPSODY ® | 5-ethyl-6-(3,5,5-trimethylhexyl)-[1,2,4]triazolo[1,5-a]pyrimidin-7-ylamine |
| No. D.117 | SERENADE ® MAX | 5-ethyl-6-(3,5,5-trimethylhexyl)-[1,2,4]triazolo[1,5-a]pyrimidin-7-ylamine |
| No. D.118 | SERENADE ® ASO | 5-ethyl-6-(3,5,5-trimethylhexyl)-[1,2,4]triazolo[1,5-a]pyrimidin-7-ylamine |
| No. D.119 | SONATA ® | 5-ethyl-6-(3,5,5-trimethylhexyl)-[1,2,4]triazolo[1,5-a]pyrimidin-7-ylamine |
| No. D.120 | BALLAD ® Plus | 5-ethyl-6-(3,5,5-trimethylhexyl)-[1,2,4]triazolo[1,5-a]pyrimidin-7-ylamine |
| No. D.121 | RHAPSODY ® | 6-octyl-5-propyl-[1,2,4]triazolo[1,5-a]pyrimidin-7-ylamine |
| No. D.122 | SERENADE ® MAX | 6-octyl-5-propyl-[1,2,4]triazolo[1,5-a]pyrimidin-7-ylamine |
| No. D.123 | SERENADE ® ASO | 6-octyl-5-propyl-[1,2,4]triazolo[1,5-a]pyrimidin-7-ylamine |
| No. D.124 | SONATA ® | 6-octyl-5-propyl-[1,2,4]triazolo[1,5-a]pyrimidin-7-ylamine |
| No. D.125 | BALLAD ® Plus | 6-octyl-5-propyl-[1,2,4]triazolo[1,5-a]pyrimidin-7-ylamine |
| No. D.126 | RHAPSODY ® | 5-methoxymethyl-6-octyl-[1,2,4]triazolo[1,5-a]pyrimidin-7-ylamine |
| No. D.127 | SERENADE ® MAX | 5-methoxymethyl-6-octyl-[1,2,4]triazolo[1,5-a]pyrimidin-7-ylamine |
| No. D.128 | SERENADE ® ASO | 5-methoxymethyl-6-octyl-[1,2,4]triazolo[1,5-a]pyrimidin-7-ylamine |
| No. D.129 | SONATA ® | 5-methoxymethyl-6-octyl-[1,2,4]triazolo[1,5-a]pyrimidin-7-ylamine |
| No. D.130 | BALLAD ® Plus | 5-methoxymethyl-6-octyl-[1,2,4]triazolo[1,5-a]pyrimidin-7-ylamine |
| No. D.131 | RHAPSODY ® | 6-octyl-5-trifluoromethyl-[1,2,4]triazolo[1,5-a]pyrimidin-7-ylamine |
| No. D.132 | SERENADE ® MAX | 6-octyl-5-trifluoromethyl-[1,2,4]triazolo[1,5-a]pyrimidin-7-ylamine |
| No. D.133 | SERENADE ® ASO | 6-octyl-5-trifluoromethyl-[1,2,4]triazolo[1,5-a]pyrimidin-7-ylamine |
| No. D.134 | SONATA ® | 6-octyl-5-trifluoromethyl-[1,2,4]triazolo[1,5-a]pyrimidin-7-ylamine |
| No. D.135 | BALLAD ® Plus | 6-octyl-5-trifluoromethyl-[1,2,4]triazolo[1,5-a]pyrimidin-7-ylamine |

TABLE 5-continued

Active compound combinations of a component 1) and a component 2), conprising a compound II selected from group D):

| Mixture | Component 1) | Component 2) |
|---|---|---|
| No. D.136 | RHAPSODY ® | 5-trifluoromethyl-6-(3,5,5-trimethylhexyl)-[1,2,4]triazolo[1,5-a]pyrimidin-7-ylamine |
| No. D.137 | SERENADE ® MAX | 5-trifluoromethyl-6-(3,5,5-trimethylhexyl)-[1,2,4]triazolo[1,5-a]pyrimidin-7-ylamine |
| No. D.138 | SERENADE ® ASO | 5-trifluoromethyl-6-(3,5,5-trimethylhexyl)-[1,2,4]triazolo[1,5-a]pyrimidin-7-ylamine |
| No. D.139 | SONATA ® | 5-trifluoromethyl-6-(3,5,5-trimethylhexyl)-[1,2,4]triazolo[1,5-a]pyrimidin-7-ylamine |
| No. D.140 | BALLAD ® Plus | 5-trifluoromethyl-6-(3,5,5-trimethylhexyl)-[1,2,4]triazolo[1,5-a]pyrimidin-7-ylamine |

TABLE 6

Active compound combinations of a component 1) and a component 2), conprising a compound II selected from group E):

| Mixture | Component 1) | Component 2) |
|---|---|---|
| No. E.1 | RHAPSODY ® | methasulphocarb |
| No. E.2 | SERENADE ® MAX | methasulphocarb |
| No. E.3 | SERENADE ® ASO | methasulphocarb |
| No. E.4 | SONATA ® | methasulphocarb |
| No. E.5 | BALLAD ® Plus | methasulphocarb |
| No. E.6 | RHAPSODY ® | propamocarb hydrochloride |
| No. E.7 | SERENADE ® MAX | propamocarb hydrochloride |
| No. E.8 | SERENADE ® ASO | propamocarb hydrochloride |
| No. E.9 | SONATA ® | propamocarb hydrochloride |
| No. E.10 | BALLAD ® Plus | propamocarb hydrochloride |

TABLE 7

Active compound combinations of a component 1) and a component 2), conprising a compound II selected from group F):

| Mixture | Component 1) | Component 2) |
|---|---|---|
| No. F.1 | RHAPSODY ® | metrafenone |
| No. F.2 | SERENADE ® MAX | metrafenone |
| No. F.3 | SERENADE ® ASO | metrafenone |
| No. F.4 | SONATA ® | metrafenone |
| No. F.5 | BALLAD ® Plus | metrafenone |
| No. F.6 | RHAPSODY ® | dodine free base |
| No. F.7 | SERENADE ® MAX | dodine free base |
| No. F.8 | SERENADE ® ASO | dodine free base |
| No. F.9 | SONATA ® | dodine free base |
| No. F.10 | BALLAD ® Plus | dodine free base |
| No. F.11 | RHAPSODY ® | guazatine-acetate |
| No. F.12 | SERENADE ® MAX | guazatine-acetate |
| No. F.13 | SERENADE ® ASO | guazatine-acetate |
| No. F.14 | SONATA ® | guazatine-acetate |
| No. F.15 | BALLAD ® Plus | guazatine-acetate |
| No. F.16 | RHAPSODY ® | iminoctadine-triacetate |
| No. F.17 | SERENADE ® MAX | iminoctadine-triacetate |
| No. F.18 | SERENADE ® ASO | iminoctadine-triacetate |
| No. F.19 | SONATA ® | iminoctadine-triacetate |
| No. F.20 | BALLAD ® Plus | iminoctadine-triacetate |
| No. F.21 | RHAPSODY ® | iminoctadine-tris(albesilate) |
| No. F.22 | SERENADE ® MAX | iminoctadine-tris(albesilate) |
| No. F.23 | SERENADE ® ASO | iminoctadine-tris(albesilate) |
| No. F.24 | SONATA ® | iminoctadine-tris(albesilate) |
| No. F.25 | BALLAD ® Plus | iminoctadine-tris(albesilate) |
| No. F.26 | RHAPSODY ® | kasugamycin-hydrochlorid-hydrat |
| No. F.27 | SERENADE ® MAX | kasugamycin-hydrochlorid-hydrat |
| No. F.28 | SERENADE ® ASO | kasugamycin-hydrochlorid-hydrat |
| No. F.29 | SONATA ® | kasugamycin-hydrochlorid-hydrat |
| No. F.30 | BALLAD ® Plus | kasugamycin-hydrochlorid-hydrat |
| No. F.31 | RHAPSODY ® | dichlorophen |
| No. F.32 | SERENADE ® MAX | dichlorophen |
| No. F.33 | SERENADE ® ASO | dichlorophen |
| No. F.34 | SONATA ® | dichlorophen |
| No. F.35 | BALLAD ® Plus | dichlorophen |
| No. F.36 | RHAPSODY ® | pentachlorophenol |
| No. F.37 | SERENADE ® MAX | pentachlorophenol |
| No. F.38 | SERENADE ® ASO | pentachlorophenol |
| No. F.39 | SONATA ® | pentachlorophenol |

TABLE 7-continued

Active compound combinations of a component 1) and a component 2), conprising a compound II selected from group F):

| Mixture | Component 1) | Component 2) |
| --- | --- | --- |
| No. F.40 | BALLAD ® Plus | pentachlorophenol |
| No. F.41 | RHAPSODY ® | N-(4-chloro-2-nitro-phenyl)-N-ethyl-4-methyl-benzenesulfonamide |
| No. F.42 | SERENADE ® MAX | N-(4-chloro-2-nitro-phenyl)-N-ethyl-4-methyl-benzenesulfonamide |
| No. F.43 | SERENADE ® ASO | N-(4-chloro-2-nitro-phenyl)-N-ethyl-4-methyl-benzenesulfonamide |
| No. F.44 | SONATA ® | N-(4-chloro-2-nitro-phenyl)-N-ethyl-4-methyl-benzenesulfonamide |
| No. F.45 | BALLAD ® Plus | N-(4-chloro-2-nitro-phenyl)-N-ethyl-4-methyl-benzenesulfonamide |
| No. F.46 | RHAPSODY ® | dicloran |
| No. F.47 | SERENADE ® MAX | dicloran |
| No. F.48 | SERENADE ® ASO | dicloran |
| No. F.49 | SONATA ® | dicloran |
| No. F.50 | BALLAD ® Plus | dicloran |
| No. F.51 | RHAPSODY ® | nitrothal-isopropyl |
| No. F.52 | SERENADE ® MAX | nitrothal-isopropyl |
| No. F.53 | SERENADE ® ASO | nitrothal-isopropyl |
| No. F.54 | SONATA ® | nitrothal-isopropyl |
| No. F.55 | BALLAD ® Plus | nitrothal-isopropyl |
| No. F.56 | RHAPSODY ® | tecnazen |
| No. F.57 | SERENADE ® MAX | tecnazen |
| No. F.58 | SERENADE ® ASO | tecnazen |
| No. F.59 | SONATA ® | tecnazen |
| No. F.60 | BALLAD ® Plus | tecnazen |
| No. F.61 | RHAPSODY ® | biphenyl |
| No. F.62 | SERENADE ® MAX | biphenyl |
| No. F.63 | SERENADE ® ASO | biphenyl |
| No. F.64 | SONATA ® | biphenyl |
| No. F.65 | BALLAD ® Plus | biphenyl |
| No. F.66 | RHAPSODY ® | bronopol |
| No. F.67 | SERENADE ® MAX | bronopol |
| No. F.68 | SERENADE ® ASO | bronopol |
| No. F.69 | SONATA ® | bronopol |
| No. F.70 | BALLAD ® Plus | bronopol |
| No. F.71 | RHAPSODY ® | diphenylamine |
| No. F.72 | SERENADE ® MAX | diphenylamine |
| No. F.73 | SERENADE ® ASO | diphenylamine |
| No. F.74 | SONATA ® | diphenylamine |
| No. F.75 | BALLAD ® Plus | diphenylamine |
| No. F.76 | RHAPSODY ® | mildiomycin |
| No. F.77 | SERENADE ® MAX | mildiomycin |
| No. F.78 | SERENADE ® ASO | mildiomycin |
| No. F.79 | SONATA ® | mildiomycin |
| No. F.80 | BALLAD ® Plus | mildiomycin |
| No. F.81 | RHAPSODY ® | oxin-copper |
| No. F.82 | SERENADE ® MAX | oxin-copper |
| No. F.83 | SERENADE ® ASO | oxin-copper |
| No. F.84 | SONATA ® | oxin-copper |
| No. F.85 | BALLAD ® Plus | oxin-copper |
| No. F.86 | RHAPSODY ® | prohexadione calcium |
| No. F.87 | SERENADE ® MAX | prohexadione calcium |
| No. F.88 | SERENADE ® ASO | prohexadione calcium |
| No. F.89 | SONATA ® | prohexadione calcium |
| No. F.90 | BALLAD ® Plus | prohexadione calcium |
| No. F.91 | RHAPSODY ® | N-(cyclopropylmethoxyimino-(6-difluoromethoxy-2,3-difluoro-phenyl)-methyl)-2-phenyl acetamide |
| No. F.92 | SERENADE ® MAX | N-(cyclopropylmethoxyimino-(6-difluoromethoxy-2,3-difluoro-phenyl)-methyl)-2-phenyl acetamide |
| No. F.93 | SERENADE ® ASO | N-(cyclopropylmethoxyimino-(6-difluoromethoxy-2,3-difluoro-phenyl)-methyl)-2-phenyl acetamide |
| No. F.94 | SONATA ® | N-(cyclopropylmethoxyimino-(6-difluoromethoxy-2,3-difluoro-phenyl)-methyl)-2-phenyl acetamide |
| No. F.95 | BALLAD ® Plus | N-(cyclopropylmethoxyimino-(6-difluoromethoxy-2,3-difluoro-phenyl)-methyl)-2-phenyl acetamide |
| No. F.96 | RHAPSODY ® | N'-(4-(4-chloro-3-trifluoromethyl-phenoxy)-2,5-dimethyl-phenyl)-N-ethyl-N-methyl formamidine |
| No. F.97 | SERENADE ® MAX | N'-(4-(4-chloro-3-trifluoromethyl-phenoxy)-2,5-dimethyl-phenyl)-N-ethyl-N-methyl formamidine |
| No. F.98 | SERENADE ® ASO | N'-(4-(4-chloro-3-trifluoromethyl-phenoxy)-2,5-dimethyl-phenyl)-N-ethyl-N-methyl formamidine |
| No. F.99 | SONATA ® | N'-(4-(4-chloro-3-trifluoromethyl-phenoxy)-2,5-dimethyl-phenyl)-N-ethyl-N-methyl formamidine |

TABLE 7-continued

Active compound combinations of a component 1) and a component 2), comprising a compound II selected from group F):

| Mixture | Component 1) | Component 2) |
|---|---|---|
| No. F.100 | BALLAD ® Plus | N'-(4-(4-chloro-3-trifluoromethyl-phenoxy)-2,5-dimethyl-phenyl)-N-ethyl-N-methyl formamidine |
| No. F.101 | RHAPSODY ® | N'-(4-(4-fluoro-3-trifluoromethyl-phenoxy)-2,5-dimethyl-phenyl)-N-ethyl-N-methyl formamidine |
| No. F.102 | SERENADE ® MAX | N'-(4-(4-fluoro-3-trifluoromethyl-phenoxy)-2,5-dimethyl-phenyl)-N-ethyl-N-methyl formamidine |
| No. F.103 | SERENADE ® ASO | N'-(4-(4-fluoro-3-trifluoromethyl-phenoxy)-2,5-dimethyl-phenyl)-N-ethyl-N-methyl formamidine |
| No. F.104 | SONATA ® | N'-(4-(4-fluoro-3-trifluoromethyl-phenoxy)-2,5-dimethyl-phenyl)-N-ethyl-N-methyl formamidine |
| No. F.105 | BALLAD ® Plus | N'-(4-(4-fluoro-3-trifluoromethyl-phenoxy)-2,5-dimethyl-phenyl)-N-ethyl-N-methyl formamidine |
| No. F.106 | RHAPSODY ® | N'-(2-methyl-5-trifluormethyl-4-(3-trimethylsilanyl-propoxy)-phenyl)-N-ethyl-N-methyl formamidine |
| No. F.107 | SERENADE ® MAX | N'-(2-methyl-5-trifluormethyl-4-(3-trimethylsilanyl-propoxy)-phenyl)-N-ethyl-N-methyl formamidine |
| No. F.108 | SERENADE ® ASO | N'-(2-methyl-5-trifluormethyl-4-(3-trimethylsilanyl-propoxy)-phenyl)-N-ethyl-N-methyl formamidine |
| No. F.109 | SONATA ® | N'-(2-methyl-5-trifluormethyl-4-(3-trimethylsilanyl-propoxy)-phenyl)-N-ethyl-N-methyl formamidine |
| No. F.110 | BALLAD ® Plus | N'-(2-methyl-5-trifluormethyl-4-(3-trimethylsilanyl-propoxy)-phenyl)-N-ethyl-N-methyl formamidine |
| No. F.111 | RHAPSODY ® | N'-(5-difluormethyl-2-methyl-4-(3-trimethylsilanyl-propoxy)-phenyl)-N-ethyl-N-methyl formamidine |
| No. F.112 | SERENADE ® MAX | N'-(5-difluormethyl-2-methyl-4-(3-trimethylsilanyl-propoxy)-phenyl)-N-ethyl-N-methyl formamidine |
| No. F.113 | SERENADE ® ASO | N'-(5-difluormethyl-2-methyl-4-(3-trimethylsilanyl-propoxy)-phenyl)-N-ethyl-N-methyl formamidine |
| No. F.114 | SONATA ® | N'-(5-difluormethyl-2-methyl-4-(3-trimethylsilanyl-propoxy)-phenyl)-N-ethyl-N-methyl formamidine |
| No. F.115 | BALLAD ® Plus | N'-(5-difluormethyl-2-methyl-4-(3-trimethylsilanyl-propoxy)-phenyl)-N-ethyl-N-methyl formamidine |

The compositions comprising the components 1) and 2), or the simultaneous, that is joint or separate, use of a component 1) and a component 2), are distinguished by excellent activity against a broad spectrum of phytopathogenic fungi in particular from the classes of the Ascomycetes, Basidiomycetes, Deuteromycetes and Peronosporomycetes (syn. Oomycetes). Some of them are systemically active and can be used in crop protection as foliar fungicides, as soil fungicides and as fungicides for seed dressing.

The compositions according to the invention are particularly important in the control of a multitude of phytopathogenic fungi on various cultivated plants, such as cereals, for example wheat, rye, barley, triticale, oats or rice; beet, for example sugar beet or fodder beet; fruits, such as pomes, stone fruits or soft fruits, for example apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; natural rubber plants or ornamental and forestry plants, such as flowers, shrubs, broad-leaved trees or evergreens, for example conifers; and on the plant propagation material, such as seeds, and the crop material of these plants.

Preferably, compounds I and compositions thereof are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative parts of the plant such as seeds and vegetative plant material such as cuttings and tubers (e. g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be mentioned. These young plants may also be protected before transplantation by a total or partial treatment by immersion or pouring.

Preferably, treatment of plant propagation materials with compounds I and compositions thereof is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering. Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant.

The term "cultivated plants" is to be understood also including plants that have been rendered tolerant to applications of specific classes of herbicides, such as hydroxyphenylpyruvate dioxygenase (HPPD) inhibitors; acetolactate synthase (ALS) inhibitors, such as sulfonyl ureas (see e. g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e. g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073); enolpyruvylshikimate-3-phosphate synthase (EPSPS) inhibitors, such as glyphosate (see e. g. WO 92/00377); glutamine synthetase (GS) inhibitors, such as glufosinate (see e. g. EP-A-0242236, EP-A-242246) or oxynil herbicides (see e. g. U.S. Pat. No. 5,559,024) as a result of conventional methods of breeding or genetic engineering. Several cultivated plants have been rendered tolerant to herbicides by conventional methods of breeding (mutagenesis), for example Clearfield® summer rape (Canola) being tolerant to imidazolinones, e. g. imazamox. Genetic engineering methods have been used to render cultivated plants, such as soybean, cotton, corn, beets and rape, tolerant to herbicides, such as glyphosate and glufosinate, some of which are commercially available under the trade names RoundupReady® (glyphosate) and LibertyLink® (glufosinate).

The term "cultivated plants" is to be understood also including plants that are by the use of recombinant DNA techniques capable to synthesize one or more insecticidal proteins, especially those known from the bacterial genus *Bacillus*, particularly from *Bacillus thuringiensis*, such as δ-endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, for example *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains. (see, for example WO 02/015701). Further examples of such toxins or genetically modified plants capable of synthesizing such toxins are disclosed, for example, in EP-A 374 753, WO 93/007278, WO 95/34656, EP-A 427 529, EP-A 451 878, WO 03/018810 und WO 03/052073. The methods for producing such genetically modified plants are generally known to the person skilled in the art and are described, for example, in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda).

Genetically modified plants capable to synthesize one or more insecticidal proteins are, for example, described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e. g. Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe SA., Belgium (cotton cultivars producing a modified version of the Cry1Ac toxin) and 1507 from Pioneer Overseas Corporation, Belgium (corn cultivars producing the Cry1F toxin and PAT enzyme).

The term "cultivated plants" is to be understood also including plants that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, for example EP-A 0 392 225), plant disease resistance genes (for example potato cultivars, which express resistance genes acting against *Phytophthora infestans* derived from the mexican wild potato *Solanum bulbocastanum*) or T4-lysozym (e. g. potato cultivars capable of synthesizing these proteins with increased resistance against bacteria such as *Erwinia amylvora*). The methods for producing such genetically modified plants are generally known to the person skilled in the art and are described, for example, in the publications mentioned above.

The term "cultivated plants" is to be understood also including plants that are by the use of recombinant DNA techniques capable to synthesize one or more proteins to increase the productivity (e. g. bio mass production, grain yield, starch content, oil content or protein content), tolerance to drought, salinity or other growth-limiting environmental factors or tolerance to pests and fungal, bacterial or viral pathogens of those plants.

The term "cultivated plants" is to be understood also including plants that contain by the use of recombinant DNA techniques a modified amount of substances of content or new substances of content, specifically to improve human or animal nutrition, for example oil crops that produce health-promoting long-chain omega-3 fatty acids or unsaturated omega-9 fatty acids (e. g. Nexera® rape).

The term "cultivated plants" is to be understood also including plants that contain by the use of recombinant DNA techniques a modified amount of substances of content or new substances of content, specifically to improve raw material production, for example potatoes that produce increased amounts of amylopectin (e. g. Amflora® potato).

The term "protein" as used herein is to be understood as an oligopeptide or polypeptide or molecule made up of polypeptides including expressly also pre-proteins, hybrid proteins, peptides, truncated or otherwise modified proteins including those derived from post-transcriptional modifications such as acylation (e.g. acetylation, the addition of an acetyl group, usually at the N-terminus of the protein), alkylation, the addition of an alkyl group (e.g. addition of ethyl or methyl, usually at lysine or arginine residues) or demethylation, amidation at C-terminus, biotinylation (acylation of conserved lysine residues with a biotin appendage), formylation, γ-carboxylation dependent on Vitamin K, glutamylation (covalent linkage of glutamic acid residues), glycosylation (addition of a glycosyl group to either asparagine, hydroxylysine, serine, or threonine, resulting in a glycoprotein), glycation (nonenzymatic attachment of sugars), glycylation (covalent linkage of one to more glycine residues), covalent attachment of a heme moiety, hydroxylation, iodination, isoprenylation (addition of an isoprenoid group such as farnesol and geranylgeraniol), lipoylation (attachment of a lipoate functionality) including prenylation, GPI anchor formation (e. g. myristoylation, farnesylation and geranylgeranylation), covalent attachment of nucleotides or derivatives thereof including ADP-ribosylation and flavin attachment, oxidation, pegylation, covalent attachment of phosphatidylinositol, phosphopantetheinylation (addition of a 4'-phosphopantetheinyl moiety from coenzyme A), phosphorylation (addition of a phosphate group, usually to serine, tyrosine, threonine or histidine), pyroglutamate formation, racemization of proline, tRNA-mediated addition of amino acids such as arginylation, sulfation (addition of a sulfate group to a tyrosine), selenoylation (co-translational incorporation of selenium in selenoproteins), ISGylation (covalent linkage to the ISG15 protein [Interferon-stimulated Gene 15]), SUMOylation (covalent linkage to the SUMO protein [Small Ubiquitin-related MOdifier]), ubiquitination (covalent linkage to the protein ubiquitin or polyubiquitin), citrullination or deimination (conversion of arginine to citrulline), deamidation (conversion of glutamine to glutamic acid or asparagine to aspartic acid), formation of disulfide bridges (covalent linkage of two cysteine amino acids) or proteolytic cleavage (cleavage of a protein at a peptide bond).

The plants or seed treated with the combinations comprising components 1) and 2) may by wildlife types, plants or seed obtained by breeding and transgenic plants as well as their seed.

They are especially suitable for controlling the following phytopathogenic fungi:

Alternaria atrans tenuissima
Alternaria brassicae
Alternaria spp.
Ascochyta tritici
Blumeria graminis
Botrytis cinerea
Bremia lactucae
Bremia lucinae
Calonectria crotalariae
Cercospora canescens
Cercospora kikuchii
Cercospora sojina
Cercospora canescens
Choanephora infundibulifera
Cladosporium herbarum
Cochliobolus sativus
Cochliobolus sativus
Colletotrichum truncatum
Corynespora cassiicola
Dactuliophora glycines
Dematophora necatrix Diaporthe phaseolorum
Diaporthe phaseolorum var. caulivora
Drechslera glycini
Epicoccum spp.
Erwinia amylovora
Erysiphe graminis
Frogeye sojina
Fusarium solani
Fusarium culmorum
Fusarium graminearum
Gaeumannomyces graminis
Leptosphaeria nodorum
Leptosphaerulina trifolii
Macrophomina phaseolina
Microdochium nivale
Microsphaera diffusa
Mycoleptodiscus terrestris
Neocosmospora vasinfecta
Pellicularia sasakii
Peronospora brassicae
Peronospora manshurica
Peronospora brassicae
Peronospora pisi
Phakopsora pachyrhizi
Phakopsora meibomiae
Phialophora gregata
Phomopsis phaseoli
Phyllostica sojaecola
Physiological leaf spots
Phythium ultimum
Phytophthora megasperma
Phytophthora infestans
Phytopthora megasperma
Plasmopara viticola
Podosphaera leucotricha
Podosphaera leucotricha
Pseudocercospora herpotrichoides
Pseudomonas lachrymans
Pseudomonas syringae
Pseudoperonospora cubensis
Pseudoperonospora humuli
Puccinia hordei
Puccinia recondita
Puccinia striiformis
Puccinia triticina
Pyrenochaeta glycines
Pyrenophora allosuri
Pyrenophora altermarina
Pyrenophora avenae
Pyrenophora bartramiae
Pyrenophora bondarzevii
Pyrenophora bromi
Pyrenophora bryophila
Pyrenophora buddleiae
Pyrenophora bupleuri
Pyrenophora calvertii
Pyrenophora calvescens var. moravica
Pyrenophora carthanie
Pyrenophora centranthi
Pyrenophora cerastii
Pyrenophora chengii
Pyrenophora chrysamthemi
Pyrenophora convohuli
Pyrenophora coppeyana
Pyrenophora cytisi
Pyrenophora dactylidis
Pyrenophora dictyoides
Pyrenophora echinopis
Pyrenophora ephemera
Pyrenophora eryngicola
Pyrenophora erythrospila
Pyrenophora euphorbiae
Pyrenophora freticola
Pyrenophora graminea
Pyrenophora graminea
Pyrenophora heraclei
Pyrenophora hordei
Pyrenophora horrida
Pyrenophora hyperici

*Pyrenophora japonica*
*Pyrenophora kugitangi*
*Pyrenophora lithophila*
*Pyrenophora lolii*
*Pyrenophora macrospora*
*Pyrenophora metasequoiae*
*Pyrenophora minuertiae hirsutae*
*Pyrenophora moravica*
*Pyrenophora moroczkowskii*
*Pyrenophora muscorum*
*Pyrenophora osmanthi*
*Pyrenophora phlei*
*Pyrenophora pimpinellae*
*Pyrenophora pittospori*
*Pyrenophora polytricha*
*Pyrenophora pontresinerisis*
*Pyrenophora pulsatillae*
*Pyrenophora raetica*
*Pyrenophora rayssiae*
*Pyrenophora rugosa*
*Pyrenophora ryohicola*
*Pyrenophora saviczii*
*Pyrenophora schoeteri*
*Pyrenophora scholevskii*
*Pyrenophora scirpi*
*Pyrenophora scirpicola*
*Pyrenophora secalis*
*Pyrenophora semeniperda*
*Pyrenophora semiusta*
*Pyrenophora seseli*
*Pyrenophora seseli* f. *poterii*
*Pyrenophora subalpina*
*Pyrenophora sudetica*
*Pyrenophora suhantarctica*
*Pyrenophora syntrichiae*
*Pyrenophora szaferiana*
*Pyrenophora teres*
*Pyrenophora teres* f. *makulata*
*Pyrenophora teres* subsp. *graminea*
*Pyrenophora tetrahenae*
*Pyrenophora tranzschelii*
*Pyrenophora trifulii*
*Pyrenophora triticil-repentis*
*Pyrenophora ushuwaiensis*
*Pyrenophora villose*
*Pyrenophora graminea*
*Pyrenophora teres*
*Pyrenophora teres*
*Pyrenophora teres*
*Pyrenophora tritici repentis*
*Pyricularia oryzae*
*Pythium aphanidermatum*
*Pythium debaryanum*
*Pythium irregulare*
*Pythium myriotylum*
*Pythium ultimum*
*Ramularia collocygni*
*Rhizoctonia aerea*
*Rhizoctonia alba*
*Rhizoctonia alpina*
*Rhizoctonia anaticula*
*Rhizoctonia anomala*
*Rhizoctonia apocynacearum*
*Rhizoctonia arachnion*
*Rhizoctonia asclerotica*
*Rhizoctonia batalicola*
*Rhizoctonia borealis*
*Rhizoctonia callae*
*Rhizoctonia carorae*
*Rhizoctonia cerealis*
*Rhizoctonia choussii*
*Rhizoctonia coniothecioides*
*Rhizoctonia cundida*
*Rhizoctonia dichoroma*
*Rhizoctonia dimorpha*
*Rhizoctonia endophytica*
*Rhizoctonia endophytica* var. *filicata*
*Rhizoctonia ferruginea*
*Rhizoctonia floccosa*
*Rhizoctonia fragariae*
*Rhizoctonia fraxini*
*Rhizoctonia fuliginea*
*Rhizoctonia fumigata*
*Rhizoctonia globularis*
*Rhizoctonia goodyerae-repentis*
*Rhizoctonia gossypii*
*Rhizoctonia gossypii* var. *anatolica*
*Rhizoctonia gracilis*
*Rhizoctonia griseo*
*Rhizoctonia hiemalis*
*Rhizoctonia juniperi*
*Rhizoctonia lamallifera*
*Rhizoctonia leguminicola*
*Rhizoctonia lilacina*
*Rhizoctonia luoini*
*Rhizoctonia macrosclerotia*
*Rhizoctonia melongenae*
*Rhizoctonia microsclerotia*
*Rhizoctonia monilioides*
*Rhizoctonia monteithiana*
*Rhizoctonia muneratii*
*Rhizoctonia nandorii*
*Rhizoctonia oryzae*
*Rhizoctonia oryzae-sativae*
*Rhizoctonia pallida*
*Rhizoctonia pini-insignis*
*Rhizoctonia praticola*
*Rhizoctonia quercus*
*Rhizoctonia ramicola*
*Rhizoctonia robusta*
*Rhizoctonia rubi*
*Rhizoctonia ruhiginosa*
*Rhizoctonia sclerotica*
*Rhizoctonia solani*
*Rhizoctonia solani* f. *paroketea*
*Rhizoctonia solani forma specialis*
*Rhizoctonia solani* var. *cedri-deodorae*
*Rhizoctonia solani* var. *fuchsiae*
*Rhizoctonia solani* var. *hortensis*
*Rhizoctonia stahlii*
*Rhizoctonia subtilis* var. *nigra*
*Rhizoctonia subtilis*
*Rhizoctonia tomato*
*Rhizoctonia tuliparum*
*Rhizoctonia veae*
*Rhizoctonia versicolor*
*Rhizoctonia cerealis*
*Rhynchosporium secalis*
*Sclerotina rolfsii*
*Sclerotinia rolfsii*
*Sclerotinia sclerotiorum*
*Septoria glycines*
*Septoria nodorum*
*Septoria tritici*
*Sphaerotheca fuliginea*
*Stagonospora nodorum*
*Stemphylium botryosum*
*Thielaviopsis basicola*
*Tilletia aegilopis*
*Tilletia aegopogonis*
*Tilletia ahamadiana*
*Tilletia airina*
*Tilletia ajrekari*
*Tilletia alopecuri*
*Tilletia anthaxanthi*
*Tilletia apludae*
*Tilletia armdinellae*
*Tilletia asperifolia*
*Tilletia asperitolioides*
*Tilletia atacamensis*
*Tilletia baldrati*
*Tilletia bambusae*
*Tilletia banarasae*
*Tilletia bangalorensis*
*Tilletia barclayana*
*Tilletia biharica*
*Tilletia boliviensis*
*Tilletia boutelouae*

*Tilletia brachypodii*
*Tilletia brachypodii-ramosi*
*Tilletia braomi-tectorum*
*Tilletia brevifaciens*
*Tilletia bromi*
*Tilletia bromina*
*Tilletia brunkii*
*Tilletia buchloeana*
*Tilletia bulayi*
*Tilletia caries*
*Tilletia cathcariae*
*Tilletia cerebrina*
*Tilletia chloridicola*
*Tilletia contaoversa*
*Tilletia contraversa* var. *prostrata*
*Tilletia contraversa* var. *elyni*
*Tilletia corona*
*Tilletia cynasuri*
*Tilletia damacarae*
*Tilletia deyeuxiae*
*Tilletia digitariicola*
*Tilletia durangensis*
*Tilletia earlei*
*Tilletia echinochlave*
*Tilletia echinochloae*
*Tilletia echinosperma*
*Tilletia ehrhartae*
*Tilletia eleusines*
*Tilletia elymandrae*
*Tilletia elymicola*
*Tilletia elyni*
*Tilletia elythrophori*
*Tilletia eragrostidis*
*Tilletia euphorbiae*
*Tilletia fahrendorfii*
*Tilletia festinca-octoflorana*
*Tilletia foelida*
*Tilletia foliicola*
*Tilletia fusca*
*Tilletia fusca* var. *bromi-tectorum*
*Tilletia fusca* var. *guyotiana*
*Tilletia fusca* var. *paragonica*
*Tilletia georfischeri*
*Tilletia gigaspora*
*Tilletia goloskokovii*
*Tilletia haynaldiae*
*Tilletia heterospora*
*Tilletia holci*
*Tilletia hordei* var. *spontanei*
*Tilletia horrida*
*Tilletia hyalospora* var. *cuzcoensis*
*Tilletia hyparrheniae*
*Tilletia indica*
*Tilletia iniermedia*
*Tilletia iovensis*
*Tilletia ixophari*
*Tilletia koeleriae*
*Tilletia kuznetzoviana*
*Tilletia laevis*
*Tilletia laguri*
*Tilletia leptochlase*
*Tilletia lepturi*
*Tilletia macrotuberculata*
*Tilletia madeirensis*
*Tilletia maglagonii*
*Tilletia makutensis*
*Tilletia milti*
*Tilletia milti-vernalis*
*Tilletia montana*
*Tilletia montemartinii*
*Tilletia nanifica*
*Tilletia narasimhanii*
*Tilletia narayanaoana*
*Tilletia narduri*
*Tilletia nigrifaciens*
*Tilletia obscura-reticulora*
*Tilletia oklahomae*
*Tilletia okudoirae*
*Tilletia oplistmeni-cristati*
*Tilletia paae*
*Tilletia pachyderma*
*Tilletia pallida*
*Tilletia panici*
*Tilletia panici. humilis*
*Tilletia paonensis*
*Tilletia paraloxa*
*Tilletia paspali*
*Tilletia pennisetina*
*Tilletia peritidis*
*Tilletia phalaridis*
*Tilletia polypoganis*
*Tilletia prostrata*
*Tilletia pulcherrima* var. *brachiariae*
*Tilletia redfieldiae*
*Tilletia rhei*
*Tilletia rugispora*
*Tilletia sabaudiae*
*Tilletia salzmanii*
*Tilletia savilei*
*Tilletia scrobiculata*
*Tilletia setariae*
*Tilletia setariae-palmiflorarae*
*Tilletia setariicola*
*Tilletia sphaerococca*
*Tilletia sphenopie*
*Tilletia sphenopodis*
*Tilletia sterilis*
*Tilletia taiana*
*Tilletia texana*
*Tilletia themedae-anatherae*
*Tilletia themedicola*
*Tilletia toguateei*
*Tilletia trachypogonis*
*Tilletia transiliensis*
*Tilletia transvaalensis*
*Tilletia tritici* f. *monococci*
*Tilletia tritici* var. *controversa*
*Tilletia tritici* var. *nanifica*
*Tilletia tritici* var. *laevis*
*Tilletia tritici-repentis*
*Tilletia triticoides*
*Tilletia tuberculare*
*Tilletia vertiveriae*
*Tilletia viermotii*
*Tilletia vittara*
*Tilletia vittara* var. *burmahnii*
*Tilletia walkeri*
*Tilletia youngii*
*Tilletia zundelii*
*Typhula incarnata*
*Uromyces appendiculatus*
*Ustilago aaeluropodis*
*Ustilago abstrusa*
*Ustilago aegilopsidis*
*Ustilago affinis* var. *hilariae*
*Ustilago agrestis*
*Ustilago agropyrina*
*Ustilago agrostis-palustris*
*Ustilago airear-caespitosae*
*Ustilago alismatis*
*Ustilago almadina*
*Ustilago alopecurivara*
*Ustilago alsineae*
*Ustilago altilis*
*Ustilago amadelpha* var. *glabriuscula*
*Ustilago amphilophidis*
*Ustilago amplexa*
*Ustilago amthoxanthi*
*Ustilago andropogonis-tectorum*
*Ustilago aneilemae*
*Ustilago anhweiona*
*Ustilago anomala* var. *avicularis*
*Ustilago anomala* var. *carnea*
*Ustilago anomala* var. *cordai*
*Ustilago anomala* var. *microspora*
*Ustilago anomala* var. *muricata*
*Ustilago anomala* var. *tovarae*
*Ustilago apscheronica*

-continued

*Ustilago arabidia. alpinae*
*Ustilago arandinellae-hirtae*
*Ustilago arctica*
*Ustilago argentina*
*Ustilago aristidarius*
*Ustilago arotragostis*
*Ustilago asparagi-pygmaei*
*Ustilago asprellae*
*Ustilago avanae* subsp. *alba*
*Ustilago avenae*
*Ustilago avenae*
*Ustilago avenae* f. sp. *perennars*
*Ustilago avenariae-bryophyllae*
*Ustilago avicularis*
*Ustilago bahuichivoensis*
*Ustilago barbari*
*Ustilago beckeropsis*
*Ustilago belgiana*
*Ustilago bethelii*
*Ustilago bicolor*
*Ustilago bistortarum ustiloginea*
*Ustilago bistortarum* var. *pustulata*
*Ustilago boreatis*
*Ustilago bothriochloae*
*Ustilago bothriochloae-intermediae*
*Ustilago bouriqueti*
*Ustilago braziliensis*
*Ustilago brisae*
*Ustilago bromi-arvensis*
*Ustilago bromi-erecti*
*Ustilago bromi-mallis*
*Ustilago bromina*
*Ustilago bromivora* f. *brachypodii*
*Ustilago bromivora* var. *microspora*
*Ustilago bullata* f. *brachypodii-distachyi*
*Ustilago bullata* var. *bonariesis*
*Ustilago bullata* var. *macrospora*
*Ustilago bungeana*
*Ustilago calanagrostidis*
*Ustilago calanagrostidis* var. *scrobiculata*
*Ustilago calanagrostidis* var. *typica*
*Ustilago cardamines*
*Ustilago cariciphila*
*Ustilago caricis-wallichianae*
*Ustilago carnea*
*Ustilago catherimae*
*Ustilago caulicola*
*Ustilago cenrtodomis*
*Ustilago ceparum*
*Ustilago cephalariae*
*Ustilago chacoensis*
*Ustilago chloridii*
*Ustilago chloridionis*
*Ustilago chrysopoganis*
*Ustilago chubulensis*
*Ustilago cichorii*
*Ustilago cilmodis*
*Ustilago clelandii*
*Ustilago clintoniana*
*Ustilago coloradensis*
*Ustilago commelinae*
*Ustilago compacta*
*Ustilago concelata*
*Ustilago condigna*
*Ustilago consimilis*
*Ustilago constantineanui*
*Ustilago controversa*
*Ustilago conventere-sexualis*
*Ustilago cordai*
*Ustilago corlarderiae* var. *araucana*
*Ustilago coronariaw*
*Ustilago coronata*
*Ustilago courtoisii*
*Ustilago crus-galli* var. *minor*
*Ustilago cryptica*
*Ustilago curta*
*Ustilago custanaica*
*Ustilago cynodontis*
*Ustilago cynodontis*

-continued

*Ustilago cyperi-lucidi*
*Ustilago davisii*
*Ustilago deccanii*
*Ustilago decipiens*
*Ustilago deformitis*
*Ustilago dehiscens*
*Ustilago delicata*
*Ustilago deyeuxiae*
*Ustilago dianthorum*
*Ustilago distichlidis*
*Ustilago dubiosa*
*Ustilago dumosa*
*Ustilago earlei*
*Ustilago echinochloae*
*Ustilago ehrhartana*
*Ustilago eleocharidis*
*Ustilago eleusines*
*Ustilago elymicola*
*Ustilago elytrigiae*
*Ustilago enneapogonis*
*Ustilago epicampida*
*Ustilago eragrostidis-japanicana*
*Ustilago eriocauli*
*Ustilago eriochloae*
*Ustilago euphorbiae*
*Ustilago fagopyri*
*Ustilago festucae*
*Ustilago festucorum*
*Ustilago filamenticola*
*Ustilago fingerhuthiae*
*Ustilago flectens*
*Ustilago flonersii*
*Ustilago foliorum*
*Ustilago formosana*
*Ustilago fueguina*
*Ustilago gageae*
*Ustilago garcesi*
*Ustilago gardneri*
*Ustilago gausenii*
*Ustilago gayazana*
*Ustilago gigantispora*
*Ustilago glyceriae*
*Ustilago gregaria*
*Ustilago grossheimii*
*Ustilago gunnerae*
*Ustilago haesendocki* var. *chloraphorae*
*Ustilago haesendocki* var. *vargasii*
*Ustilago halophiloides*
*Ustilago haynalodiae*
*Ustilago heleochloae*
*Ustilago helictotrichi*
*Ustilago herteri* var. *Bicolor*
*Ustilago herteri* var. *vargasii*
*Ustilago hierochloae-adoratae*
*Ustilago hieronymi* var. *insularis*
*Ustilago hieronymi* var. *minor*
*Ustilago hilariicola*
*Ustilago hilubii*
*Ustilago himalensis*
*Ustilago histortarum* var. *marginalis*
*Ustilago hitchcockiana*
*Ustilago holci-avanacei*
*Ustilago hordei*
*Ustilago hordei* f. sp. *avenae*
*Ustilago hsuii*
*Ustilago hyalino-bipolaris*
*Ustilago hydropiperis*
*Ustilago hyparrheniae*
*Ustilago hypodyies* f. *congoensis*
*Ustilago hypodytes* f. *sporaboli*
*Ustilago hypodytes* var. *agrestis*
*Ustilago idonea*
*Ustilago imperatue*
*Ustilago induia*
*Ustilago inouyei*
*Ustilago intercedens*
*Ustilago iranica*
*Ustilago isachnes*
*Ustilago ischaemi-akoensis*

*Ustilago ischaemi-anthephoroides*
*Ustilago ixiolirii*
*Ustilago ixophori*
*Ustilago jacksonii*
*Ustilago jacksonii* var. *vintonesis*
*Ustilago jaczevskyana*
*Ustilago jaczevskyana* van. *typica*
*Ustilago jaczevskyana* var. *sibirica*
*Ustilago jagdishwari*
*Ustilago jamalainentii*
*Ustilago jehudana*
*Ustilago johnstonii*
*Ustilago kairamoi*
*Ustilago kasuchstemica*
*Ustilago kenjiana*
*Ustilago kweichowensis*
*Ustilago kylingae*
*Ustilago lacjrymae-jobi*
*Ustilago lepyrodiclidis*
*Ustilago lidii*
*Ustilago liebenbergii*
*Ustilago linderi*
*Ustilago linearis*
*Ustilago lirove*
*Ustilago loliicola*
*Ustilago longiflora*
*Ustilago longiseti*
*Ustilago longissima* var. *dubiosa*
*Ustilago longissima* var. *paludificans*
*Ustilago longissima* var. *typica*
*Ustilago lupini*
*Ustilago lychnidis-dioicae*
*Ustilago lycoperdiformis*
*Ustilago lyginiae*
*Ustilago machili*
*Ustilago machringiae*
*Ustilago magalaspora*
*Ustilago magellanica*
*Ustilago mariscana*
*Ustilago maydis*
*Ustilago melicae*
*Ustilago merxmuellerana*
*Ustilago mesatlantica*
*Ustilago michnoana*
*Ustilago microspora*
*Ustilago microspora* var. *paspalicola*
*Ustilago microstegii*
*Ustilago microthelis*
*Ustilago milli*
*Ustilago mobtagnei* var. *minor*
*Ustilago modesta*
*Ustilago moenchiae-manticae*
*Ustilago monermae*
*Ustilago morinae*
*Ustilago morobiana*
*Ustilago mrucata*
*Ustilago muda*
*Ustilago muehlenbergiae* var. *lucumanensis*
*Ustilago muscaribotryoidis*
*Ustilago nagarnyi*
*Ustilago nannfeldtii*
*Ustilago nauda* var. *hordei*
*Ustilago nelsoniana*
*Ustilago nepalensis*
*Ustilago neyraudiae*
*Ustilago nigra*
*Ustilago nivalis*
*Ustilago nuda*
*Ustilago nuda*
*Ustilago nuda* var. *tritici*
*Ustilago nyassae*
*Ustilago okudairae*
*Ustilago olida*
*Ustilago olivacea* var. *macrospora*
*Ustilago onopordi*
*Ustilago onumae*
*Ustilago opiziicola*
*Ustilago oplismeni*
*Ustilago orientalis*
*Ustilago otophora*
*Ustilago ovariicola*
*Ustilago overcemii*
*Ustilago pamirica*
*Ustilago panici-geminati*
*Ustilago panjabensis*
*Ustilago pappophori*
*Ustilago pappophori* var. *magdalensis*
*Ustilago parasnothii*
*Ustilago parodii*
*Ustilago parvula*
*Ustilago paspalidiicola*
*Ustilago patagonica*
*Ustilago penniseti* var. *verruculosa*
*Ustilago perrara*
*Ustilago persicariae*
*Ustilago petrakii*
*Ustilago phalaridis*
*Ustilago phlei*
*Ustilago phlei-protensis*
*Ustilago phragmites*
*Ustilago picacea*
*Ustilago pimprina*
*Ustilago piperi* (var.) *rosulata*
*Ustilago poae*
*Ustilago poae-bulbosae*
*Ustilago poae-nemoralis*
*Ustilago polygoni-alati*
*Ustilago polygoni-alpini*
*Ustilago polygoni-punctari*
*Ustilago polygoni-serrulati*
*Ustilago polytocae*
*Ustilago polytocae-harbatas*
*Ustilago pospelovii*
*Ustilago prostrata*
*Ustilago pseudohieronymi*
*Ustilago puehlaensis*
*Ustilago puellaris*
*Ustilago pulvertulensa*
*Ustilago raciborskiana*
*Ustilago radians*
*Ustilago ravida*
*Ustilago rechingeri*
*Ustilago reticulara*
*Ustilago reticulispora*
*Ustilago rhei*
*Ustilago rhynchelytri*
*Ustilago ruandenis*
*Ustilago ruberculata*
*Ustilago sabouriana*
*Ustilago salviae*
*Ustilago sanctae-catharinae*
*Ustilago scaura*
*Ustilago scillae*
*Ustilago scitaminea*
*Ustilago scitaminea* var. *sacchar-officinorum*
*Ustilago scleranthi*
*Ustilago scrobiculata*
*Ustilago scutulata*
*Ustilago secalis* var. *elymi*
*Ustilago seitaminea* var. *sacchari-barberi*
*Ustilago semenoviana*
*Ustilago serena*
*Ustilago serpens*
*Ustilago sesleriae*
*Ustilago setariae-mambassanae*
*Ustilago shastensis*
*Ustilago shimadae*
*Ustilago silenes-inflatae*
*Ustilago silenes-nutantis*
*Ustilago sinkiangensis*
*Ustilago sitanil*
*Ustilago sleuneri*
*Ustilago sonoriana*
*Ustilago sorghi-stipoidei*
*Ustilago spadicea*
*Ustilago sparoboli-indici*
*Ustilago sparti*
*Ustilago speculariae*

-continued

Ustilago spegazzinii
Ustilago spegazzinii var. agrestis
Ustilago spermophora var. orientalis
Ustilago spermophoroides
Ustilago spinulosa
Ustilago sporoboli-trenuli
Ustilago stellariae
Ustilago sterilis
Ustilago stewartli
Ustilago stipae
Ustilago striaeformis f. phlei
Ustilago striaeformis f. poa . . .
Ustilago striaeformis f. poae-pratensis
Ustilago striiformis f. hierochloes-odoratae
Ustilago striiformis var. agrostidis
Ustilago striiformis var. dactylidis
Ustilago striiformis var. holci
Ustilago striiformis var. phlei
Ustilago striiformis var. poae
Ustilago sumnevicziana
Ustilago superha
Ustilago sydowiana
Ustilago symbiotica
Ustilago taenia
Ustilago taiana
Ustilago tanakue
Ustilago tenuispora
Ustilago thaxteri
Ustilago tinontiae
Ustilago togata
Ustilago tournenxii
Ustilago tovarae
Ustilago trachophora var. pacifica
Ustilago trachyniae
Ustilago trachypogonis
Ustilago tragana
Ustilago tragi
Ustilago tragica
Ustilago tragi-racemosi
Ustilago trichoneurana
Ustilago trichophora var. crus-galli
Ustilago trichophora var. panici-frumentacei
Ustilago triseti
Ustilago tritici forma specialis
Ustilago tucumariensis
Ustilago tumeformis
Ustilago turcomanica
Ustilago turcomanica var. prostrata
Ustilago turcomanica var. typica
Ustilago ugamica
Ustilago ugandensis var. macrospora
Ustilago underwoodii
Ustilago urginede
Ustilago urochloana
Ustilago ustilaginea
Ustilago ustriculosa var. cordai
Ustilago ustriculosa var. reticulata
Ustilago valentula
Ustilago vavilori
Ustilago verecunda
Ustilago verruculosa
Ustilago versatilis
Ustilago vetiveriae
Ustilago violaceo-irregularis
Ustilago violaceu var. stellariae
Ustilago violaceuverrucosa
Ustilago williamsii
Ustilago wynaadensis
Ustilago zambettakisii
Ustilago zernae
Venturia inaequalis
Xanthomonas campestris
Xanthomonas oryzae The compositions comprising the components 1) and 2) are particularly suitable for controlling phytopathogenic fungi in barley (e.g. *Pyrenophora teres, Rhynchosporium secalis, Puccinia hordei, Puccinia striiformis, Blumeria graminis, Ramularia collo-cygni*/Physiological leaf spots,

*Microdochium nivale, Typhula incamata, Pseudocercosporella herpotrichoides, Fusarium culmorum, Rhizoctonia cerealis, Gaeumannomyces graminis*) and soybeans (e.g. *Phakopsora pachyrhizi, Microsphaera diffusa, Septoria glycines, Cercospora sojina, Cercospora kikuchii, Corynespora cassiicola, Colletotrichum truncatum, Peronospora manshurica, Alternaria* spp., *Phomopsis phaseoli, Diaporthe phaseolorum, Phialophora gregata, Fusarium solani, Sclerotinia sclerotiorum, Sclerotinia rolfsii, Phytopthora megasperma, Rhizoctonia solani, Dematophora necatrix, Macrophomina phaseolina*).

The inventive compositions are particularly suitable for controlling phytopathogenic fungi in soybeans, vegetables and fruit crops.

The compositions according to the invention are furthermore suitable for controlling harmful fungi in the protection of materials (for example wood, paper, paint dispersions, fibers or fabrics) and in the protection of stored products. In the protection of wood, particular attention is paid to the following harmful fungi: Ascomycetes, such as *Ophiostoma* spp., *Ceratocystis* spp., *Aureobasidium pullulans, Scierophoma* spp., *Chaetomium* spp., *Humicola* spp., *Petriella* spp., *Trichurus* spp.; Basidiomycetes, such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes, such as *Aspergillus* spp., *Cladosporium* spp., *Penicillium* spp., *Trichoderma* spp., *Alternaria* spp., *Paecilomyces* spp. and *Zygomycetes*, such as *Mucor* spp., additionally in the protection of materials the following yeasts: *Candida* spp. and *Saccharomyces cerevisae.*

Application of the inventive compositions to useful plants may also lead to an increase in the crop yield.

The components 1) and 2) can be applied simultaneously, that is jointly or separately, or in succession, the sequence, in the case of separate application, generally not having any effect on the result of the control measures.

When preparing the compositions, it is preferred to employ the commercially available formulations of components 1) and 2), to which further compounds active against harmful fungi or other pests, such as insects, arachnids or nematodes, or else herbicidal or growth-regulating active compounds or fertilizers may be added.

Usually, compositions comprising component 1) and 2), wherein component 2) consists of only one active ingredient (II), are employed. However, in certain cases compositions wherein component 2) consists of two or, if appropriate, more active components may be advantageous.

Suitable further active components in the above sense are in particular the active compounds II mentioned at the outset, and in particular the preferred active compounds II mentioned above.

Components 1) and 2) are usually employed in a weight ratio of from 100:1 to 1:100, preferably from 30:1 to 1:30, in particular from 15:1 to 1:15.

The further active components are, if desired, added in a ratio of from 20:1 to 1:20 to component 1).

Depending on the particular components and the desired effect, the application rates for component 1) are generally from 1 l to 100 l broth containing the strain per hectare, preferably from 1; to 50 l/ha, in particular from 1 to 20 l/ha.

Correspondingly, the application rates for component 2) are generally from 1 to 2000 g/ha, preferably from 10 to 1500 g/ha, in particular from 40 to 1000 g/ha.

The method for controlling harmful fungi is carried out by the separate or joint application of a component 1) and a component 2), or a composition comprising components 1)

and 2), by spraying or dusting the seeds, the plants or the soils before or after sowing of the plants or before or after emergence of the plants.

The compositions according to the invention, or the single components separately, can be converted into customary formulations, for example solutions, emulsions, suspensions, dusts, powders, pastes and granules. The use form depends on the particular intended purpose; in each case, it should ensure a fine and even distribution of the mixture according to the invention.

The formulations are prepared in a known manner, for example by extending the single components with solvents and/or carriers, if desired using emulsifiers and dispersants. Solvents/auxiliaries suitable for this purpose are essentially:

water, aromatic solvents (for example Solvesso® products, xylene), paraffins (for example mineral oil fractions), alcohols (for example methanol, butanol, pentanol, benzyl alcohol), ketones (for example cyclohexanone, gamma-butyrolactone), pyrrolidones (N-methylpyrrolidone, N-octylpyrrolidone), acetates (glycol diacetate), glycols, fatty acid dimethylamides, fatty acids and fatty acid esters. In principle, solvent mixtures may also be used.

carriers such as ground natural minerals (for example kaolins, clays, talc, chalk) and ground synthetic minerals (for example highly disperse silica, silicates); emulsifiers such as nonionogenic and anionic emulsifiers (for example polyoxyethylene fatty alcohol ethers, alkylsulfonates and arylsulfonates) and dispersants such as lignosulfite waste liquors and methylcellulose.

Suitable surfactants used are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl sulfoxide, N-methylpyrrolidone and water.

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In order to achieve good dispersion and adhesion of compositions within the present invention, it may be advantageous to formulate the whole broth culture, supernatant and/or metabolite with components that aid dispersion and adhesion.

In general, the formulations comprise from 0.01 to 95% by weight, preferably from 0.1 to 90% by weight, of the components.

The active compounds (II) are employed in a purity of from 90% to 100%, preferably 95% to 100% (according to NMR spectrum).

The following are examples of formulations: 1. Products for dilution with water

A) Water-Soluble Concentrates (SL)

10 parts by weight of a composition according to the invention are dissolved in 90 parts by weight of water or in a water-soluble solvent. As an alternative, wetting agents or other auxiliaries are added. Dilution with water results in a formulation having a content of 10% by weight of components 1) and 2) is obtained.

B) Dispersible Concentrates (DC)

20 parts by weight of a composition according to the invention are dissolved in 70 parts by weight of cyclohexanone with addition of 10 parts by weight of a dispersant, for example polyvinylpyrrolidone. Dilution with water gives a dispersion having a content of 0% by weight of components 1) and 2).

C) Emulsifiable Concentrates (EC)

15 parts by weight of a composition according to the invention are dissolved in 75 parts by weight of xylene with addition of calcium dodecylbenzenesulfonate and castor oil ethoxylate (in each case 5 parts by weight). Dilution with water gives an emulsion. The formulation has a content of 15% by weight of components 1) and 2).

D) Emulsions (EW, EO)

25 parts by weight of a composition according to the invention are dissolved in 35 parts by weight of xylene with addition of calcium dodecylbenzenesulfonate and castor oil ethoxylate (in each case 5 parts by weight). This composition is introduced into 30 parts by weight of water by means of an emulsifying machine (Ultraturrax) and made into a homogeneous emulsion. Dilution with water gives an emulsion. The formulation has a content of 25% by weight of components 1) and 2).

E) Suspensions (SC, OD)

In an agitated ball mill, 20 parts by weight of a composition according to the invention are comminuted with addition of 10 parts by weight of dispersants and wetting agents and 70 parts by weight of water or an organic solvent to give a fine suspension. Dilution with water gives a stable suspension having a content of 20% by weight of components 1) and 2).

F) Water-Dispersible Granules and Water-Soluble Granules (WG, SG)

50 parts by weight of a composition according to the invention are ground finely with addition of 50 parts by weight of dispersants and wetting agents and prepared as water-dispersible or water-soluble granules by means of technical appliances (for example extrusion, spray tower, fluidized bed). Dilution with water gives a stable dispersion or solution having a content of 50% by weight of components 1) and 2).

G) Water-Dispersible Powders and Water-Soluble Powders (WP, SP)

75 parts by weight of a composition according to the invention are ground in a rotor-stator mill with addition of 25 parts by weight of dispersants, wetting agents and silica gel. Dilution with water gives a stable dispersion or solution having a content of 75% by weight of components 1) and 2).

2. Products to be Applied Undiluted

H) Dustable Powders (DP)

5 parts by weight of a composition according to the invention are ground finely and mixed intimately with 95 parts by weight of finely divided kaolin. This gives a dustable product having a content of 5% by weight of components 1) and 2).

J) Granules (GR, FG, GG, MG)

0.5 part by weight of a composition according to the invention is ground finely and associated with 99.5 parts by weight of carriers. Current methods are extrusion, spray-drying or the fluidized bed. This gives granules to be applied undiluted having a content of 0.5% of weight of components 1) and 2).

K) ULV Solutions (UL)

10 parts by weight of a composition according to the invention are dissolved in 90 parts by weight of an organic solvent, for example xylene. This gives a product to be applied undiluted having a compound content of 10% by weight of components 1) and 2).

Components 1) and 2) can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of components 1) and 2) according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetting agent, tackifier, dispersant or emulsifier. However, it is also possible to prepare concentrates composed of active substance, wetting agent, tackifier, dispersant or emulsifier and, if appropriate, solvent or oil, and such concentrates are suitable for dilution with water.

The concentrations of the components in the ready-to-use preparations can be varied within relatively wide ranges. In general, they are from 0.0001 to 100%, preferably from 0.01 to 100%.

Components 1) and 2) may also be used successfully in the ultra-low-volume process (ULV), it being possible to apply formulations comprising over 95% by weight of active compound, or even to apply components 1) and 2) without additives.

Oils of various types, wetting agents or adjuvants may be added to the component 1) or 2), even, if appropriate, not until immediately prior to use (tank mix). These agents are typically admixed with component 1) or 2) according to the invention in a weight ratio of from 1:100 to 100:1, preferably from 1:10 to 10:1.

Suitable adjuvants in this sense are in particular: organically modified polysiloxanes, for example Break Thru S 240®; alcohol alkoxylates, for example Atplus 245®, Atplus MBA 1303®, Plurafac LF 300® and Lutensol ON 30®; EO/PO block polymers, for example Pluronic RPE 2035® and Genapol B®; alcohol ethoxylates, for example Lutensol XP 80®; and sodium dioctylsulfosuccinate, for example Leophen RA®.

Components 1) and 2) or the composition comprising components 1) and 2), or the corresponding formulations, are applied by treating the harmful fungi, the plants, seeds, soils, areas, materials or spaces to be kept free from them with a fungicidally effective amount of the composition or, in the case of separate application, of the components 1) and 2) separately. Application can be before or after the infection by harmful fungi.

The fungicidal action of components 1) and 2) and of the compositions according to the invention was demonstrated by the tests below.

Components 1) and 2), separately or jointly, were prepared as a stock solution comprising 25 mg of active compound which was made up to 10 ml using a mixture of acetone and/or DMSO and the emulsifier Uniperol® EL (wetting agent having an emulsifying and dispersing action based on ethoxylated alkylphenols) in a ratio by volume of solvent/emulsifier of 99:1. The mixture was then made up to 100 ml with water. This stock solution was diluted with the solvent/emulsifier/water mixture described to give the concentration of active compound stated below.

The visually determined percentages of infected leaf areas were converted into efficacies in % of the untreated control:

The efficacy (E) is calculated as follows using Abbot's formula:

$$E=(1-\alpha/\beta)\cdot 100$$

α corresponds to the fungicidal infection of the treated plants in % and

β corresponds to the fungicidal infection of the untreated (control) plants in %

An efficacy of 0 means that the infection level of the treated plants corresponds to that of the untreated control plants; an efficacy of 100 means that the treated plants were not infected.

The expected efficacies of active compound combinations were determined using Colby's formula (Colby, S. R. "Calculating synergistic and antagonistic responses of herbicide combinations", Weeds, 15, pp. 20-22, 1967) and compared with the observed efficacies.

$$E=x+y-x\cdot y/100 \qquad \text{Colby's formula:}$$

E expected efficacy, expressed in % of the untreated control, when using the mixture of the active compounds A and B at the concentrations a and b x efficacy, expressed in % of the untreated control, when using the active compound A at the concentration a y efficacy, expressed in % of the untreated control, when using the active compound B at the concentration b

The invention claimed is:

1. A fungicidal composition for controlling phytopathogenic harmful fungi, comprising 1) *Bacillus subtilis* strain with NRRL Accession No. B-21661 or a mutant thereof having all the identifying characteristics of the strain, and 2) at least one chemical compound (II), wherein chemical compound (II) is a carboxamide selected from the group consisting of N-(cis-2-bicyclopropyl-2-yl-phenyl)-3-difluoromethyl-1-methyl-1H-pyrazole-4-carboxamide, N-(trans-2-bicyclopropyl-2-yl-phenyl)-3-difluoromethyl-1-methyl-1H-pyrazole-4-carboxamide, and combinations thereof in a synergistically effective amount.

2. The fungicidal composition according to claim 1, comprising as component 1) a commercially available formulation of the *Bacillus subtilis* strain with NRRL Accession No. B-21661 or mutant thereof having all the identifying characteristics of the strain.

3. The fungicidal composition according to claim 1, wherein component 1) is the *Bacillus subtilis* strain with NRRL Accession No. B-21661.

4. The fungicidal composition according to claim 1 comprising as component 2) N-(cis-2-bicyclopropyl-2-yl-phenyl)-3-difluoromethyl-1-methyl-1H-pyrazole-4-carboxamide and N-(trans-2-bicyclopropyl-2-yl-phenyl)-3-difluoromethyl-1-methyl-1H-pyrazole-4-carboxamide.

5. The fungicidal composition according to claim 1, comprising an additional active compound V, selected from the groups G) to M):

G) azoles selected from the group consisting of bitertanol, bromuconazole, cyproconazole, difenoconazole, diniconazole, enilconazole, epoxiconazole, fluquinconazole, fenbuconazole, flusilazole, flutriafol, hexaconazole, imiben-conazole, ipconazole, metconazole, myclobutanil, penconazole, propiconazole, prothioconazole, simeconazole, triadimefon, triadimenol, tebuconazole, tetraconazole, triticonazole, prochloraz, pefurazoate, imazalil, triflumizole, cyazofamid, benomyl, carbendazim, thiabendazole, fuberidazole, ethaboxam, etridiazole and hymexazole;

H) strobilurins selected from the group consisting of azoxystrobin, dimoxy-strobin, enestroburin, fluoxastrobin, kresoxim-methyl, methominostrobin, orysastrobin, picoxystrobin, pyraclostrobin, trifloxystrobin, enestroburin, methyl (2-chloro-5-[1-(3-methylbenzyloxyimino)ethyl]benzyl)carbamate, methyl (2-chloro-5-[1-(6-methylpyridin-2-ylmethoxyimino)ethyl]benzyl)-carbamate and methyl 2-(ortho-(2,5-dimethylphenyloxymethylene)phenyl)-3-methoxyacrylate;

J) carboxamides selected from the group consisting of carboxin, boscalid, fenhexamid, flutolanil, furametpyr, mepronil, metalaxyl, mefenoxam, ofurace, oxadixyl, oxycarboxin, penthiopyrad, thifluzamide, tiadinil, 3,4-dichloro-N-(2-cyanophenyl)isothiazole-5-carboxamide, dimethomorph, flumorph, flumetover, fluopicolide (picobenzamid), zoxamide, carpropamid, diclocymet, mandipropamid, N-(2-(4-[3-(4-chlorophenyl)prop-2-ynyloxy]-3-methoxy-phenyl)ethyl)-2-methanesulfonylamino-3-methylbutyramide, N-(2-(4-[3-(4-chlorophenyl)prop-2-ynyloxy]-3-methoxyphenyl)ethyl)-2-ethanesulfonyl-amino-3-methylbutyramide, methyl 3-(4-chlorophenyl)-3-(2-isopropoxy-carbonylamino-3-methylbutyrylamino)propionate, N-(4'-bromobiphenyl-2-yl)-4-difluoromethyl-2-methylthiazole-5-carboxamide, N-(4'-trifluoromethyl-biphenyl-2-yl)-4-difluoromethyl-2-methylthiazole-5-carboxamide, N-(4'-chloro-3'-fluorobiphenyl-2-yl)-4-difluoromethyl-2-methyl-thiazole-5-carboxamide, N-(3',4'-dichloro-4-fluorobiphenyl-2-yl)-3-difluoro-methyl-1-methylpyrazole-4-carboxamide, N-(3',4'-dichloro-5-fluorobiphenyl-2-yl)-3-difluoromethyl-1-methylpyrazole-4-carboxamide and N-(2-cyanophenyl)-3,4-dichloro-isothiazole-5-carboxamide;

K) heterocyclic compounds selected from the group consisting of fluazinam, pyrifenox, bupirimate, cyprodinil, fenarimol, ferimzone, mepanipyrim, nuarimol, pyrimethanil, triforine, fenpiclonil, fludioxonil, aldimorph, dodemorph, fenpropimorph, tridemorph, fenpropidin, iprodione, procymidone, vinclozolin, famoxadone, fenamidone, octhilinone, probenazole, anilazine, diclomezine, pyroquilon, proquinazid, tricyclazole, 2-butoxy-6-iodo-3-propylchromen-4-one, acibenzolar-S-methyl, captafol, captan, dazomet, folpet, fenoxanil, quinoxyfen and N,N-dimethyl-3-(3-bromo-6-fluoro-2-methylindole-1-sulfonyl)-[1,2,4]triazole-1-sulfonamide;

L) carbamates selected from the group consisting of mancozeb, maneb, metam, metiram, ferbam, propineb, thiram, zineb, ziram, diethofencarb, iprovalicarb, flubenthiavalicarb, propamocarb, 4-fluorophenyl N-(1-(1-(4-cyanophenyl)ethanesulfonyl)but-2-yl)carbamate, methyl 3-(4-chlorophenyl)-3-(2-isopropoxycarbonylamino-3-methyl-butyrylamino)propanoate and carbamate oxime ethers of the formula VI

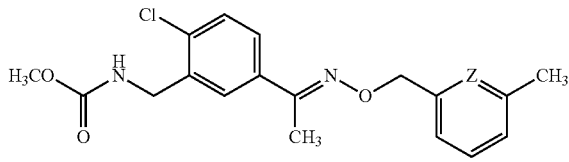

in which Z is N or CH;

M) other fungicides selected from the group consisting of guanidine, dodine, iminoctadine, guazatine, antibiotics: kasugamycin, streptomycin, polyoxin, validamycin A, nitrophenyl derivatives: binapacryl, dinocap, dinobuton, sulfur-containing heterocyclyl compounds: dithianon, isoprothiolane, organometallic compounds: fentin salts, organophosphorus compounds: edifenphos, iprobenfos, fosetyl, fosetyl-aluminum, phosphorous acid and its salts, pyrazophos, tolclofos-methyl, organochlorine compounds: chlorothalonil, dichlofluanid, flusulfamide, hexachlorobenzene, phthalide, pencycuron, quintozene, thiophanate-methyl, tolylfluanid, inorganic active compounds: Bordeaux mixture, copper acetate, copper hydroxide, copper oxychloride, basic copper sulfate, sulfur, others: cyflufenamid, cymoxanil, dimethirimol, ethirimol, furalaxyl and spiroxamine.

6. The fungicidal composition according to claim 1, comprising the components 1) and 2) in a weight ratio of from 100:1 to 1:100.

7. A fungicidal agent, comprising at least one liquid or solid carrier and a composition according to claim 1.

8. A method for controlling phytopathogenic harmful fungi, wherein the fungi, their habitat or the plants to be protected against fungal attack, the soil, seed, areas, materials or spaces are/is treated with an effective amount of a fungicidal composition according to claim 1.

9. The method according to claim 8, wherein components 1) and 2) are applied simultaneously, that is jointly or separately, or in succession.

10. A seed comprising a fungicidal composition according to claim 1.

11. The method of claim 8, wherein the components 1) and 2) are present in a weight ratio of from 100:1 to 1:100.

12. The method of claim 8, wherein the composition further comprises at least one liquid or solid carrier.

13. A method for controlling harmful fungi, wherein a transgenic plant or the seed thereof is treated with a fungicidal agent suitable for controlling harmful fungi comprising a fungicidal composition according to claim 1.

14. The method of claim 13, wherein components 1) and 2) are applied simultaneously, that is jointly or separately, or in succession.

15. The method of claim 13, wherein the components 1) and 2) are present in a weight ratio of from 100:1 to 1:100.

16. The method of claim 13, wherein the composition further comprises at least one liquid or solid carrier.

17. The method of claim 13, wherein component 2) is N-(cis-2-bicyclopropyl-2-yl-phenyl)-3-difluoromethyl-1-methyl-1H-pyrazole-4-carboxamide and N-(trans-2-bicyclopropyl-2-yl-phenyl)-3-difluoromethyl-1-methyl-1H-pyrazole-4-carboxamide.

18. The method of claim 8, wherein component 2) is N-(cis-2-bicyclopropyl-2-yl-phenyl)-3-difluoromethyl-1-methyl-1H-pyrazole-4-carboxamide and N-(trans-2-bicyclopropyl-2-yl-phenyl)-3-difluoromethyl-1-methyl-1H-pyrazole-4-carboxamide.

\* \* \* \* \*